United States Patent
Grilló Dolset et al.

(10) Patent No.: US 11,707,515 B2
(45) Date of Patent: Jul. 25, 2023

(54) MODIFIED *BRUCELLA* VACCINE STRAIN FOR THE TREATMENT OF BRUCELLOSIS

(71) Applicants: CONSEJO SUPERIOR DE INVESTIGACIONES CIENTÍFICAS (CSIC), Madrid (ES); UNIVERSIDAD PÚBLICA DE NAVARRA, Pamplona (ES)

(72) Inventors: María Jesús Grilló Dolset, Aranguren (ES); Beatriz San Román Aberasturi, Aranguren (ES); Leyre Palacios Chaves, Aranguren (ES); Sara Mena Bueno, Aranguren (ES); Ana Zabalza Baranguá, Aranguren (ES)

(73) Assignees: CONSEJO SUPERIOR DE INVESTIGACIONES CIENTÍFICAS (CSIC), Madrid (ES); UNIVERSIDAD PÚBLICA DE NAVARRA, Pamplona (ES)

( * ) Notice: Subject to any disclaimer, the term of this patent is extended or adjusted under 35 U.S.C. 154(b) by 0 days.

(21) Appl. No.: 17/687,313

(22) Filed: Mar. 4, 2022

(65) Prior Publication Data

US 2022/0273785 A1 Sep. 1, 2022

Related U.S. Application Data

(63) Continuation of application No. 16/766,629, filed as application No. PCT/EP2018/082539 on Nov. 26, 2018, now Pat. No. 11,298,416.

(30) Foreign Application Priority Data

Nov. 24, 2017 (EP) .................................... 17382798

(51) Int. Cl.
  *A61K 39/02* (2006.01)
  *A61P 31/04* (2006.01)
  *A61K 39/00* (2006.01)

(52) U.S. Cl.
  CPC ............ *A61K 39/098* (2013.01); *A61P 31/04* (2018.01); *A61K 2039/522* (2013.01)

(58) Field of Classification Search
  None
  See application file for complete search history.

(56) References Cited

U.S. PATENT DOCUMENTS

| | | | |
|---|---|---|---|
| 10,683,493 | B2 | 6/2020 | Clapés Saborit et al. |
| 10,907,135 | B2 | 2/2021 | Redondo Moya et al. |
| 2017/0184576 | A1 | 6/2017 | Esteve Tintó et al. |
| 2020/0345701 | A1 | 11/2020 | López Serrano et al. |
| 2021/0181189 | A1 | 6/2021 | Esteve Tintó et al. |
| 2021/0330662 | A1 | 10/2021 | Alcázar González et al. |
| 2021/0363501 | A1 | 11/2021 | Redondo Moya et al. |
| 2022/0135640 | A1 | 5/2022 | Delgado Mora et al. |

FOREIGN PATENT DOCUMENTS

| | | |
|---|---|---|
| EP | 2 508 201 A1 | 10/2012 |
| WO | 2017/108515 A1 | 6/2017 |

OTHER PUBLICATIONS

Pardon et al (Ann. Rech Vet. 1990. 21: 153-160).*
Adone et al., "Evaluation of *Brucella melitensis* B115 as rough-phenotype vaccines against *B. ovis* infections," *Vaccine* 26:4913-4917, 2008.
Baldwin et al., "Host Immune Responses to the Intracellular Bacteria *Brucella*: Does the Bacteria Instruct the Host to Facilitate Chronic Infection?," *Critical Reviews in Immunology* 26(5):407-442, Feb. 2006.
Barrio et al., "Rough mutants defective in core and O-polysaccharide synthesis and export induce antibodies reacting in an indirect ELISA with smooth lipopolysaccharide and are less effective than Rev 1 vaccine against *Brucella melitensis* infection of sheep," *Vaccine* 27:1741-1749, 2009.
Chacón-Diaz et al., "The use of green fluorescent protein as a marker for *Brucella* vaccines," *Vaccine* 29:577-582, 2011.
Cloekaert et al., "O-chain expression in the rough *Brucella miletensis* strain B115: induction of O-polysaccharide-specific monoclonal antibodies and intracellular localization demonstrated by immunoelectron microscopy," *Journal of General Microbiology* 138:1211-1219, 1992.
Conde-Álvarez et al., "The Lipopolysaccharide Core of *Brucella abortus* Acts as a Shield Against Innate Immunity Recognition," *PLoS Pathogens* 8(5):e1002675, 2012.
Curina et al., "Evaluation of immune responses in mice and sheep inoculated with a live attenuated *Brucella melitensis* REV 1 vaccine produced in bioreactor," *Veterinary Immunology and Immunopathology* 198:44-53, Feb. 22, 2018.
De Miguel et al., "Development of a Selective Culture Medium for Primary Isolation of the Main *Brucella* Species," *Journal of Clinical Microbiology* 49(4):1458-1463, 2011.
Godfroid et al., "Genetic organization of the lipopolysaccharide O-antigen biosynthesis region of *Brucella melitensis* 16M (wbk)," *Res. Microbiol.* 151:655-668, 2000.
González et al., "Brucellosis Vaccines: Assessment of *Brucella melitensis* Lipopolysaccharide Rough Mutants Defective in Core and O-Polysaccharide Synthesis and Export," *PLoS One* 3(7):e2760, 2008 (16 pages).

(Continued)

*Primary Examiner* — Jennifer E Graser
(74) *Attorney, Agent, or Firm* — Seed Intellectual Property Law Group LLP

(57) ABSTRACT

The present application provides a modified *Brucella* strain, its use as a medicament, and its use as a medicament for the treatment and/or prevention of brucellosis. The *Brucella* strain has been modified through an inactivation of the wzm gene. Further, the present application provides a pharmaceutical composition which comprises the modified *Brucella* strain, its use as a medicament, and its use as a medicament for the treatment and/or prevention of brucellosis. The present application also provides a kit which comprises the modified *Brucella* strain and a pharmaceutically acceptable carrier or diluent and its use for the treatment and/or prevention of brucellosis.

12 Claims, 15 Drawing Sheets

Specification includes a Sequence Listing.

(56) References Cited

OTHER PUBLICATIONS

Grilló et al., "Efficacy of bp26 and bp26/omp31 *B. melitensis* Rev.1 deletion mutants against *Brucella ovis* in rams," *Vaccine 27*:187-191, 2009 (6 pages).
Grilló et al., "Efficacy of several antibiotic combinations against *Brucella melitensis* Rev 1 experimental infection in BALB/c mice," *Journal of Antimicrobial Chemotherapy 58*:622-626, 2006.
Grilló et al., "In Vitro Markers and Biological Activity in Mice of Seed Lot Strains and Commercial *Brucella melitensis* Rev 1 and *Brucella abortus* B19 Vaccines," *The International Association for Biologicals 28*:119-127, 2000.
Grilló et al., "What have we learned from brucellosis in the mouse model?" *Veterinary Research 43*:29, 2012 (35 pages).
Guilloteau et al., "Nramp1 Is Not a Major Determinant in the Control of *Brucella melitensis* Infection in Mice," Infection and Immunology 71(2):621-628, Feb. 2003.
Herzberg et al., "Immunization Against *Brucella* Infection: I. Isolation and Characterization of a Streptomycin-Dependent Mutant," *Journal of Bacteriology 66*:585-599, 1953.
Herzberg et al., "Immunization Against *Brucella* Infection: II. Effectiveness of a Streptomycin-Dependent Strain of *Brucella melitensis," Journal of Bacteriology 66*:600-605, 1953.
Llobet et al., "*Klebsiella pneumoniae* OmpA Confers Resistance to Antimicrobial Peptides," *Antimicrobial Agents and Chemotherapy 53*(1):298-302, 2009.
Moriyón et al., "Rough vaccines in animal brucellosis: Structural and genetic basis and present status," *Vet. Res. 35*:1-38, 2004.
Muñoz et al., "Efficacy of Several Serological Tests and Antigens for Diagnosis of Bovine Brucellosis in the Presence of False-Positive Serological Results Due to *Yersinia enterocolitica* O:9," *Clinical and Diagnostic Laboratory Immunology 12*(1):141-151, 2005.
Perkins et al., "Towards a *Brucella* Vaccine for Humans," *FEMS Microbiol Rev 34*:379-394, 2010.
Sancho et al., "Evaluation in mice of *Brucella ovis* attenuated mutants for use as live vaccines against *B. ovis* infection," *Veterinary Research 45*(61) 2014. (10 pages).
Schurig et al., "Biological properties of RB51; a stable rough strain of *Brucella abortus," Veterinary Microbiology 28*:171-188, 1991.
Wang et al., "Effects of partial deletion of the wzm and wzt genes on lipopolysaccharide synthesis and virulence of *Brucella abortus* S19," *Molecular Medicine Reports 9*:2521-2527, 2014.
Wang et al., "Immunogenic response induced by wzm and wzt gene deletion mutants from *Brucella abortus* S19," *Molecular Medicine Reports 9*:653-658, 2014.

* cited by examiner

A)

B)

C)

E)

F)

G)

H)

Rev1    Rev1Δwzm 16M    16MΔwzm

Rev1Δwzm serum vs. *B. abortus* 2308

Rev1Δwzm serum vs. *B. melitensis* H38

Rev1Δwzm serum vs. *B. ovis* PA

SEQUENCE LISTING

<160> NUMBER OF SEQ ID NOS: 9

<210> SEQ ID NO 1

-continued

```
<211> LENGTH: 783
<212> TYPE: DNA
<213> ORGANISM: Artificial Sequence
<220> FEATURE:
<223> OTHER INFORMATION: wzm gene

<400> SEQUENCE: 1
atgatatcgt atatggctaa tgtctggaag gtacgccact tctggtggca cctttcaatg     60
tctgatttac gtgggcgctt caggcggtcc tccttgggaa tattatgggc agttatacag    120
ccactagcgc tcacgctgct actgtctttc gtgttttcta aattgttgaa tcaaagtata    180
tctgcatatg cccctatat tctatctggg attattatct gggaatacat atcatttaca     240
gtggttggtg gctaacagc gcttgtgcaa gccgatgcat atataaagca aaccagaaat    300
cctcttgcaa tttacacgct taggaacact gtttctggct tggtcgtatt atccgtagca    360
agtatctccc tattcgggtg ggtacttatc atgtttcctg aaaacttctc gctttcatgg    420
ttagcaatac caactttgct acccatcctt gctttgatag tttggccgct tgccacaatc    480
gtcggctaca tcgcgcaag atttcgagat ctgccgaatg ctctggcgct cgtgttacag    540
gcagcttggt ttgtttcgcc ggtctatttt aaagaatcga tgttcaggca gggtggattg    600
aatgcattcg ttgattataa ccctatttac cacgtgatgc agattctaag agccctgtc     660 ctttatgggg aatggcctac ggctaccaat tacatttggt gcttaggtgt gagcctcctc    720
ctaacctgcg tggcagtagc tgtggggatg cgtgcggaga agagagccat tttttaccta    780
tga                                                                  783

<210> SEQ ID NO 2
<211> LENGTH: 20
<212> TYPE: DNA
<213> ORGANISM: Artificial Sequence
<220> FEATURE:
<223> OTHER INFORMATION: F1

<400> SEQUENCE: 2
gcaaattgaa atggcagatg                                                 20

<210> SEQ ID NO 3
<211> LENGTH: 20
<212> TYPE: DNA
<213> ORGANISM: Artificial Sequence
<220> FEATURE:
<223> OTHER INFORMATION: R4

<400> SEQUENCE: 3
atgaaacgtg gcgttagtcc                                                 20

<210> SEQ ID NO 4
<211> LENGTH: 20
<212> TYPE: DNA
<213> ORGANISM: Artificial Sequence
<220> FEATURE:
<223> OTHER INFORMATION: R5

<400> SEQUENCE: 4
gcgtgtaaat tgcaagagga                                                 20

<210> SEQ ID NO 5
<211> LENGTH: 18
<212> TYPE: DNA
<213> ORGANISM: Artificial Sequence
<220> FEATURE:
<223> OTHER INFORMATION: R2
```

```
<400> SEQUENCE: 5
agcgcccacg taaatcag                                                18

<210> SEQ ID NO 6
<211> LENGTH: 37
<212> TYPE: DNA
<213> ORGANISM: Artificial Sequence
<220> FEATURE:
<223> OTHER INFORMATION: F3

<400> SEQUENCE: 6
ctgatttacg tgggcgctta acctgcgtgg cagtagc                           37

<210> SEQ ID NO 7
<211> LENGTH: 22
<212> TYPE: DNA
<213> ORGANISM: Artificial Sequence
<220> FEATURE:
<223> OTHER INFORMATION: F9

<400> SEQUENCE: 7
atgatatcgt atatggctaa tg                                           22

<210> SEQ ID NO 8
<211> LENGTH: 25
<212> TYPE: DNA
<213> ORGANISM: Artificial Sequence
<220> FEATURE:
<223> OTHER INFORMATION: rrnBP1-F

<400> SEQUENCE: 8
gttgcgcggt cagaaaatta tttta                                        25

<210> SEQ ID NO 9
<211> LENGTH: 25
<212> TYPE: DNA
<213> ORGANISM: Artificial Sequence
<220> FEATURE:
<223> OTHER INFORMATION: Gfp_F-R2

<400> SEQUENCE: 9
ttatttgtat agttcatcca tgcca                                        25
```

MODIFIED *BRUCELLA* VACCINE STRAIN FOR THE TREATMENT OF BRUCELLOSIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_210260_401C1.txt. The text file is 2.88 KB, was created on Mar. 3, 2022, and is being submitted electronically via EFS-Web.

BACKGROUND

Technical Field

The present invention can be included in the field of new therapeutics for the treatment and/or prevention of brucellosis. Specifically, the present application relates to a new vaccine strain of the genus *Brucella*. The strain can be used as a medicament, specifically for the treatment and/or prevention of brucellosis.

Description of the Related Art

Brucellosis is a zoonotic disease. In animals, *Brucella* infection causes abortions, infertility, decreased production and limitations to the trading of animals and animal products. In addition, the bacteria are transmitted from infected animals to humans, thereby inflicting a debilitating and often disabling disease, against which there is no vaccine and whose treatment requires high doses of antibiotics for prolonged periods with frequent relapses.

Therefore, brucellosis is a significant public health problem. It has been shown that the prevalence of human brucellosis is directly related to the prevalence of animal brucellosis. Thus, and in the absence of vaccines for use in humans, prevention of the disease requires the control of the infection in animals. In most socio-economic contexts, the only feasible way to control brucellosis is through programs based on the vaccination of farm animals, either through mass vaccination programs or through programs for the vaccination, diagnosis and slaughter of infected animals.

The reference vaccines against animal brucellosis are the smooth (S) strains *Brucella abortus* S19 for cattle and *Brucella melitensis* Rev1 for sheep and goats (OIE Terrestrial Manual, 2016—chapters 2.4.3. and 2.7.2). Both are live attenuated vaccines, adjuvant-free, with a low cost of production and acquisition, and highly effective against infection by field strains in ruminants (main source of infection for humans). However, a technical drawback is that they generate an immune response after vaccination indistinguishable from that induced after virulent infection by field strains, generating a problem for differentiating between infected and vaccinated animals (DIVA). To solve this problem, numerous scientific efforts have been made. One strategy has consisted in the development of rough (R) strains of *Brucella*, which, due to the absence of the O-Polysaccharide (O-PS) of lipopolysaccharide (LPS)—a known virulence factor of *Brucella* and the main antigen used in tests for serological diagnosis of infection—has led to attenuated strains usable as live vaccines, which do not significantly interfere in the serological diagnostic tests. In this context, in the 90's, the spontaneous mutant with an R phenotype known as *B. abortus* RB51 was developed by subculturing (Schurig et al., 1991. Veterinary Microbiology, 28: 171-188). Strain RB51 has been used in some countries against bovine brucellosis, with controversial results. Both RB51 and a collection of R mutants derived from *B. melitensis* genetically well characterized in the different LPS synthesis pathways (Godfroid et al., 2000. Res Microbiol, 151: 655-668; González et al., 2008. PLoS One, 3(7): e2760), reduce interference problems in the serological diagnosis of virulent infection, due to the absence of O-PS antigen. However, it has been shown that R vaccines are not ideal, because the protection they confer against virulent infections is well below that of the reference vaccines *B. abortus* S19 and *B. melitensis* Rev1 (Gonzalez et al., 2008. PLoS One, 3(7): e2760; Barrio et al., 2009. Vaccine, 27: 1741-1749).

On the other hand, bacterial tagging with the xenogenic protein Green Fluorescent Protein (GFP) has been proposed to solve the DIVA problem (Chacón-Diaz et al., 2011. Vaccine. 29(3): 577-82).

Moreover, current vaccines also have other issues such as to induce abortions and to be present in the milk of adult animals previously vaccinated (OIE Terrestrial Manual, 2016—chapters 2.4.3. and 2.7.2), to generate human infections and, in the case of *B. melitensis* Rev1, to be resistant to streptomycin (antibiotic of choice). Therefore, there is currently a need for an effective brucellosis vaccine and/or therapeutic which does not have all of the aforementioned drawbacks.

It is an objective of the present invention to provide a superior *Brucella* strain for the treatment and/or prevention of brucellosis.

BRIEF DESCRIPTION OF THE SEVERAL VIEWS OF THE DRAWINGS

FIG. 12: Bacterial killing experiment. Heat-treated (referred to as Serum-treated in the Figure) and untreated immune sera from lambs vaccinated with Rev1Δwzm was incubated for 18 h at 37° C., and 10% $CO_2$ with *B. melitensis* H38 and *B. abortus* 2308 virulent infections. The results were expressed as the standardized percentage of bacteria counts with respect to initial count in the inocula. The immune sera from lambs treated with Rev1Δwzm were capable of killing either *B. melitensis* H38, *B. abortus* 2308 or *B. ovis* PA.

SUMMARY OF THE INVENTION

Figure 1:
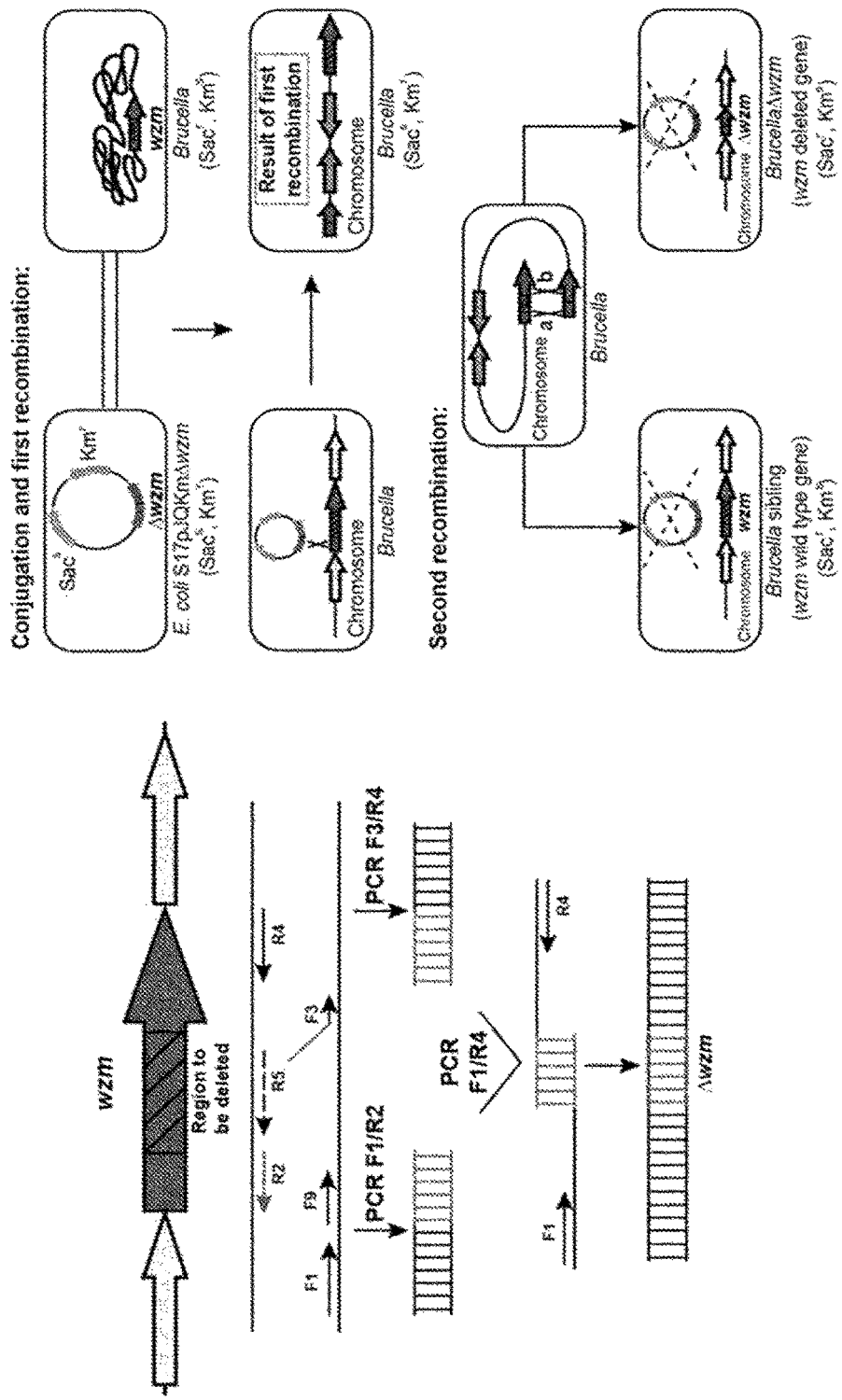
FIG. 1: Diagram showing the strategy for the deletion method by in-frame double recombination used to obtain the *Brucella*Δwzm and sibling (non-mutated) strains.

The present application provides a modified *Brucella* strain, its use as a medicament, and its use as a medicament for the treatment and/or prevention of brucellosis. The *Brucella* strain has been modified through an inactivation of the wzm gene. Further, the present application provides a pharmaceutical composition which comprises the modified *Brucella* strain, its use as a medicament, and its use as a medicament for the treatment and/or prevention of brucellosis. The present application also provides a kit which comprises the modified *Brucella* strain and a pharmaceutically acceptable carrier or diluent and its use for the treatment and/or prevention of brucellosis.

DETAILED DESCRIPTION

Definitions

The terms "treatment" and "therapy," as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

The term "prevention," as used in the present application, refers to a set of hygienic, pharmacological, surgical and/or physical means used to prevent the onset and/or development of a disease and/or symptoms. The term "prevention" encompasses prophylactic methods, since these are used to maintain the health of an animal or individual.

The term "therapeutically effective amount" refers to an amount of matter which has a therapeutic effect and which is able to treat and/or prevent brucellosis.

The term "brucellosis" refers to an infectious disease caused by bacteria from the genus *Brucella*. Brucellosis may occur in individuals or animals.

The terms "individual," "patient" or "subject" are used interchangeably in the present application and are not meant to be limiting in any way. The "individual," "patient" or "subject" can be of any age, sex and physical condition. The term "animal," as used in the present application, refers to any multicellular eukaryotic heterotroph which is not a human.

The term "vaccine," as used in the present application, refers to both "therapeutic vaccines," which are intended to treat an existing disease and/or infection by strengthening the body's natural immune response, and "prophylactic vaccines," which are intended to prevent a disease and/or infection from developing in a healthy individual or animal.

The term "modified" refers to any matter which has been altered from its original form. In the present application, the term "modified" refers to any alteration which relies on human intervention.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. In a preferred embodiment, the pharmaceutically acceptable carrier or diluent is Phosphate Buffered Saline (PBS). Preferably, the pH of the PBS is 6.85

The term "pharmaceutically acceptable adjuvant" refers to any and all substances which enhance the body's immune response to an antigen. Non-limiting examples of pharmaceutically acceptable adjuvants are: Alum, Freund's Incomplete Adjuvant, MF59, synthetic analogs of dsRNA such as poly(I:C), bacterial LPS, bacterial flagellin, imidazolquinolines, oligodeoxynucleotides containing specific CpG motifs, fragments of bacterial cell walls such as muramyl dipeptide and Quil-A®.

Modified *B. melitensis* Rev1 Strain

In a first aspect, the present application provides a modified *Brucella melitensis* Rev1 strain, wherein the wzm gene has been inactivated.

*Brucella melitensis* Rev1 is a strain which was spontaneously attenuated and obtained from the virulent strain *B. melitensis* 6056, through successive spontaneous mutations associated with streptomycin (Str) dependence and the subsequent reversal of that dependency (Herzberg and Elberg 1953. Journal of Bacteriology 66: 585-599; Herzberg and Elberg 1953. Journal of Bacteriology 66: 600-605). The Rev1 strain has been used worldwide since the 50's as the only effective vaccine to prevent brucellosis in small ruminants, and is internationally considered the standard vaccine to control ovine and caprine brucellosis (OIE Terrestrial Manual, 2016—chapters 2.4.3. and 2.7.2). The original seed lots of Rev1 are available at the Brucellosis Reference Laboratory of the OIE of AFSSA (94706 Maisons-Alfort, France) or at the European Pharmacopoeia (BP 907, 67029 Strasbourg Cedex 1, France). Further, the Rev1 strain is commercially available and can be bought from various vendors. For example, the strain can be bought from CZV Veterinaria in Spain under the name "CZV Rev1."

The wzm gene encodes for part of the two-component ABC transporter system required to export the O-PS to the periplasm where the O-PS is then assembled onto a core moiety to generate a S-LPS. The wzm gene may have the following sequence (SEQ ID NO: 1):

ATGATATCGTATATGGCTAATGTCTGGAAGGTACGCCACTTCTGGTGGC

ACCTTTCAATGTCTGATTTACGTGGGCGCTTCAGGCGGTCCTCCTTGGG

AATATTATGGGCAGTTATACAGCCACTAGCGCTCACGCTGCTACTGTCT

TTCGTGTTTTCTAAATTGTTGAATCAAAGTATATCTGCATATGCCCCCT

ATATTCTATCTGGGATTATTATCTGGGAATACATATCATTTACAGTGGT

TGGTGGCTCAACAGCGCTTGTGCAAGCCGATGCATATATAAAGCAAACC

AGAAATCCTCTTGCAATTTACACGCTTAGGAACACTGTTTCTGGCTTGG

TCGTATTATCCGTAGCAAGTATCTCCCTATTCGGGTGGGTACTTATCAT

GTTTCCTGAAAACTTCTCGCTTTCATGGTTAGCAATACCAACTTTGCTA

CCCATCCTTGCTTTGATAGTTTGGCCGCTTGCCACAATCGTCGGCTACA

TCGGCGCAAGATTTCGAGATCTGCCGAATGCTCTGGCGCTCGTGTTACA

GGCAGCTTGGTTTGTTTCGCCGGTCTATTTTAAAGAATCGATGTTCAGG

CAGGGTGGATTGAATGCATTCGTTGATTATAACCCTATTTACCACGTGA

TGCAGATTCTAAGAGCCCCTGTCCTTTATGGGGAATGGCCTACGGCTAC

CAATTACATTTGGTGCTTAGGTGTGAGCCTCCTCCTAACCTGCGTGGCA

GTAGCTGTGGGGATGCGTGCGGAGAAGAGAGCCATTTTTTACCTATGA

The wzm gene may be inactivated through any form of genetic modification known in the art. The inactivation may involve the partial or complete deletion of the gene from the host genome. The inactivation may involve a single nonesense mutation which renders the expressed protein non-functional. The inactivation may involve the mutation and/or deletion of the promoter, ribosome binding site or other transcriptional regulators which are involved in the transcription of the wzm gene. The inactivation may involve the insertion of a sequence which causes a frame shift and/or makes the resultant nascent protein non-functional. Any of the aforementioned deletions, insertions or mutations can be performed using allelic exchange (Hmelo et al., 2015. Nature Protocols, 10(11): 1820-41) or by using the CRISPR/Cas9 system (Wang et al., 2016. ACS Synthetic Biology, 5(7): 721-32). In a preferred embodiment, the wzt gene is not inactivated.

In a preferred embodiment, the inactivation of the wzm gene is due to a partial deletion of the gene. Preferably, the partial deletion involves the deletion of at least 50, 60 or 70% of SEQ ID NO: 1. More preferably, the partial deletion involves the deletion of at least 80% of SEQ ID NO: 1. In a preferred embodiment, the inactivation of the wzm gene is not achieved by inserting a transposon into the coding sequence of the gene.

In the Examples of the present invention, nucleotides 80-721 of SEQ ID NO: 1 have been deleted in *B. melitensis* Rev1 and 16M using the allelic exchange plasmid pJQKmΔwzm, which generates the correspondent Δwzm mutants (FIG. 1). Therefore, in a preferred embodiment, the inactivation of the wzm gene is achieved through the deletion of nucleotides 80-721 of SEQ ID NO: 1.

In a preferred embodiment, the modified *B. melitensis* Rev1 strain has been further modified to inactivate znuA, norD, bip, tcpB, cgs, ricA, bvrR, bvrS, one or more of the genes encoding the virB type IV secretion system selected from the group consisting of the *B. melitensis* 16M ORFs: BMEII0025, BMEII0026, BMEII0027, BMEII0028, BMEII0029, BMEII0030, BMEII0031, BMEII0032, BMEII0033, BMEII0034, and BMEII0035, and/or one or more of the genes involved in the formation, modification and/or assembly of LPS and/or metabolic pathways, including but not limited to ppdK, wbdR, gmd, manA, manB, manC, per, pgm, wbkA, wbkB, wbkC, wbkD, wbkF, wadC, and wzt (chromosomic regions wbk, wbo and wad).

In a preferred embodiment, the modified *B. melitensis* Rev1 strain has been further modified so that the autologous N-formyltransferase activity has been suppressed and a heterologous gene encoding a N-acyltransferase other than a N-formyltransferase enzyme is functionally expressed. For example, the wbkC may be inactivated and a heterologous wbdR may be introduced and expressed in the strain (see WO 2017/108515 A1).

In a preferred embodiment, the modified *B. melitensis* Rev1 strain has been further modified to express a fluorescent protein, preferably GFP. The expression of the fluorescent protein in the modified strain could be used to further distinguish Rev1 inoculated individuals or animals from infected individuals or animals (Chacón-Diaz et al., 2011. Vaccine. 29(3): 577-82; EP 2 508 201 A1). Briefly, this approach can be described as follows: when an individual or animal is vaccinated with the further modified strain, antibodies will be raised against the modified strain as well as the fluorescent protein. The antibodies raised against the fluorescent protein can be used in a serological test to test whether the individual or animal has been infected with a naturally occurring *Brucella* strain or with the further modified strain of the present invention. Thus, a kit which comprises the modified *B. melitensis* Rev1 strain which has been further modified to express a fluorescent protein may further comprise antibodies which bind to the fluorescent protein, and/or the fluorescent protein. Preferably, the fluorescent protein is GFP.

In a preferred embodiment, the strain has been lyophilized. Lyophilization can be used to increase the stability and shelf-life of the strain.

In a second aspect, the present invention provides a pharmaceutical composition which comprises the modified strain in accordance with any of the previously disclosed embodiments and a pharmaceutically acceptable carrier or diluent and/or a pharmaceutically acceptable adjuvant.

In a preferred embodiment, the pharmaceutical composition comprises the modified *B. melitensis* Rev1 strain which has been further modified to express a fluorescent protein.

A pharmaceutical composition as described herein may also contain other substances. These substances include, but are not limited to, cryoprotectants, lyoprotectants, surfactants, bulking agents, anti-oxidants, and stabilizing agents. In some embodiments, the pharmaceutical composition may be lyophilized.

The term "cryoprotectant" as used herein, includes agents which provide stability to the strain against freezing-induced stresses, by being preferentially excluded from the strain's surface. Cryoprotectants may also offer protection during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

In one embodiment, a lyoprotectant is added to a pharmaceutical composition described herein. The term "lyoprotectant" as used herein, includes agents that provide stability to the strain during the freeze-drying or dehydration process (primary and secondary freeze-drying cycles), by providing an amorphous glassy matrix and by binding with the strain's surface through hydrogen bonding, replacing the water molecules that are removed during the drying process. This helps to minimize product degradation during the lyophilization cycle, and improve the long-term product stability. Non-limiting examples of lyoprotectants include sugars, such as sucrose or trehalose; an amino acid, such as monosodium glutamate, non-crystalline glycine or histidine; a methylamine, such as betaine; a lyotropic salt, such as magnesium sulfate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a pharmaceutical composition is generally an amount that does not lead to an unacceptable amount of degradation of the strain when the pharmaceutical composition is lyophilized.

In some embodiments, a bulking agent is included in the pharmaceutical composition. The term "bulking agent" as used herein, includes agents that provide the structure of the freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the strain stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in formulations in an amount from 0.5% to 10%.

Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

In a preferred embodiment, the pharmaceutical composition further comprises an adjuvant. Preferably, the adjuvant is selected from the list consisting of Alum Hydroxide, Freund's Incomplete Adjuvant, MF59®, synthetic analogs of dsRNA such as poly(I:C), bacterial LPS, bacterial flagellin, imidazolquinolines, oligodeoxynucleotides containing specific CpG motifs, fragments of bacterial cell walls such as muramyl dipeptide and Quil-A®.

The pharmaceutical composition may be prepared for oral, sublingual, buccal, intravenous, intramuscular, subcutaneous, intraperitoneal, conjunctival, rectal, transdermal, topical and/or inhalation-mediated administration. In a preferred embodiment, the pharmaceutical composition may be a solution which is suitable for intravenous, intramuscular, conjunctival, transdermal, intraperitoneal and/or subcutaneous administration. In another embodiment, the pharmaceutical composition may be a solution which is suitable for sublingual, buccal and/or inhalation-mediated administration routes. In an alternative embodiment, the pharmaceutical composition may be an aerosol which is suitable for inhalation-mediated administration. In a preferred embodiment, the pharmaceutical composition may be prepared for subcutaneous and/or intraperitoneal administration.

The pharmaceutical composition may further comprise common excipients and carriers which are known in the state of the art. For solid pharmaceutical compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For solution for injection, the pharmaceutical composition may further comprise cryoprotectants, lyoprotectants, surfactants, bulking agents, anti-oxidants, stabilizing agents and pharmaceutically acceptable carriers. For aerosol administration, the pharmaceutical compositions are generally supplied in finely divided form along with a surfactant and propellant. The surfactant must, of course, be nontoxic, and is generally soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. For suppositories, traditional binders and carriers may include, for example, polyalkalene glycols or triglycerides.

In a preferred embodiment, the pharmaceutical composition is a vaccine capable of inducing an immune response. The design of pharmaceutical compositions for vaccines is well established, and is described, for example, in Remington's Pharmaceutical Sciences, latest edition, Mack Publishing Co., Easton, Pa., and in Plotkin and Orenstein's book entitled Vaccines, 4th Ed., Saunders, Philadelphia, Pa. (2004).

Medical Uses of the Modified Rev1 Strain

In a third aspect, the strain or pharmaceutical composition of the present invention can be used as a medicament. In a fourth aspect, the modified strain or pharmaceutical composition of the present invention can be used to treat and/or prevent brucellosis.

In a preferred embodiment, the infectious agent causing brucellosis is selected from the group consisting of *B. abortus, B. melitensis, B. suis, B. ovis, B. canis, B. neotomae, B. microti, B. ceti* and *B. pinnipedialis*. Preferably, the infectious agent causing brucellosis is selected from the group consisting of *B. abortus, B. melitensis* and *B. ovis*.

In a preferred embodiment, the strain or pharmaceutical composition is used to treat and/or prevent brucellosis in humans, cattle, goats, sheep, pigs, and/or dogs. Preferably, the strain or pharmaceutical composition is used to treat and/or prevent brucellosis in goats and/or sheep.

In a preferred embodiment, the individual or animal is inoculated with at least $10^4$ CFU (colony forming units) of the strain. Preferably, the individual or animal is inoculated with at least $10^5$, $10^6$, $10^7$, $10^8$, $10^9$, $10^{10}$, $10^{11}$ or $10^{12}$ CFU of the strain. More preferably, the individual or animal is inoculated with at least $10^9$ CFU of the strain. In an alternative embodiment, the individual or animal is inoculated with $10^4$ to $10^{12}$ CFU of the strain.

In a preferred embodiment, the strain or pharmaceutical composition is administered subcutaneously, intradermally, intravenously, intraperitoneally, by mucosae and/or conjunctively. Preferably, the strain or pharmaceutical composition is administered subcutaneously. In an alternative embodiment, the pharmaceutical composition is administered via a conjunctival administration.

In a preferred embodiment, the strain or pharmaceutical composition is used to prevent brucellosis. In this embodiment, the strain or pharmaceutical is administered as a prophylactic vaccine. Preferably, the strain or pharmaceutical composition is administered to an individual or animal who/which is at risk of becoming infected with bacteria of the genus *Brucella.*

In one embodiment, the modified strain or pharmaceutical composition is used to treat brucellosis. In a preferred embodiment, the treatment of brucellosis also involves the administration of a drug. Embodiments where the drug is administered at the same time or at different times as the modified strain or pharmaceutical composition are also envisioned. The drug may be selected from the group consisting of corticosteroids, penicillins, cephalosporins, macrolides, chloramphenicol, tetracyclines, aminoglycosides, trimethoprim, rifampin, quinolones and sulfamethoxazole.

Kit Comprising the Modified Rev1 Strain

In a fifth aspect, the present invention provides a kit comprising (i) a modified *B. melitensis* Rev1 strain, wherein the wzm gene has been inactivated and (ii) a pharmaceutically acceptable carrier or diluent.

The modified strain may be in accordance with any of the aforementioned embodiments outlined in this application. Further, the pharmaceutically acceptable carrier or diluent may be any of the aforementioned pharmaceutically acceptable carriers or diluents described in this application. In a preferred embodiment, the kit comprises instructions on how to combine the strain with the pharmaceutically acceptable carrier or diluent.

In a preferred embodiment, the modified strain is a lyophilisate. The lyophilisate may be contained in a separate container from the pharmaceutically acceptable carrier or diluent. Further, the kit may comprise instructions on how to combine the lyophilized strain with the pharmaceutically acceptable carrier or diluent.

In a preferred embodiment, the kit may further comprise an adjuvant. Preferably the adjuvant is selected from a list consisting of Alum, Freund's Incomplete Adjuvant, MF59, synthetic analogs of dsRNA such as poly(I:C), bacterial LPS, bacterial flagellin, imidazolquinolines, oligodeoxynucleotides containing specific CpG motifs, fragments of bacterial cell walls such as muramyl dipeptide and Quil-A®.

In a preferred embodiment, the instructions included with the kit may also outline the administration of the strain to an individual or animal. The outline of the administration may include the dosage to be used, the frequency of administration and/or the administration route to be used.

In a sixth aspect, the present invention provides the use of any of the described kits for the treatment and/or prevention of brucellosis. The use of the kit may be in line with any of the medical uses and methods of administration outlined in this application.

Modified *B. melitensis* 16M Strain

In a seventh aspect, the present application provides a modified *B. melitensis* 16M strain, wherein the wzm gene has been inactivated.

"*B. melitensis* 16M" is well characterized and freely available at the American Type Culture Collection (ATCC 23456).

The wzm gene may be inactivated through any form of genetic modification known in the art. The inactivation may involve the partial or complete deletion of the gene from the host genome. The inactivation may involve a single nonesense mutation which renders the expressed protein non-functional. The inactivation may involve the mutation and/or deletion of the promoter, ribosome binding site or other transcriptional regulators which are involved in the transcription of the wzm gene. The inactivation may involve the insertion of a sequence which causes a frame shift and/or makes the resultant nascent protein non-functional. Any of the aforementioned deletions, insertions or mutations can be performed using allelic exchange (Hmelo et al., 2015. Nature Protocols, 10(11): 1820-41) or by using the CRISPR/Cas9 system (Wang et al., 2016. ACS Synthetic Biology, 5(7): 721-32). In a preferred embodiment, the wzt gene is not inactivated.

In a preferred embodiment, the inactivation of the wzm gene is due to a partial deletion of the gene. Preferably, the partial deletion involves the deletion of at least 50, 60 or 70% of SEQ ID NO: 1. More preferably, the partial deletion involves the deletion of at least 80% of SEQ ID NO: 1. In a preferred embodiment, the inactivation of the wzm gene is not achieved by inserting a transposon into the coding sequence of the gene.

In a preferred embodiment, the inactivation of the wzm gene is achieved through the deletion of nucleotides 80-721 of SEQ ID NO: 1.

In a preferred embodiment, the modified *B. melitensis* 16M strain has been further modified to inactivate znuA, norD, bip, tcpB, cgs, ricA, bvrR, bvrS, one or more of the genes encoding the virB type IV secretion system selected from the group consisting of the *B. melitensis* 16M ORFs: BMEII0025, BMEII0026, BMEII0027, BMEII0028, BMEII0029, BMEII0030, BMEII0031, BMEII0032, BMEII0033, BMEII0034, and BMEII0035, and/or one or more of the genes involved in the formation, modification and/or assembly of LPS and/or metabolic pathways, including but not limited to ppdK, wbdR, gmd, manA, manB, manC, per, pgm, wbkA, wbkB, wbkC, wbkD, wbkF, wadC, and wzt (chromosomic regions wbk, wbo and wad).

In a preferred embodiment, the modified *B. melitensis* 16M strain has been further modified so that the autologous N-formyltransferase activity has been suppressed and a heterologous gene encoding a N-acyltransferase other than a N-formyltransferase enzyme is functionally expressed. For example, the wbkC may be inactivated and a heterologous wbdR may be introduced and expressed in the strain (see WO 2017/108515 A1).

In a preferred embodiment, the modified *B. melitensis* 16M strain has been further modified to express a fluorescent protein, preferably GFP. The expression of the fluorescent protein in the modified strain could be used to further distinguish 16M inoculated individuals or animals from infected individuals or animals (Chacón-Diaz et al., 2011. Vaccine. 29(3): 577-82; EP 2 508 201 A1). Thus, a kit which comprises the modified *B. melitensis* 16M strain which has been further modified to express a fluorescent protein may further comprise antibodies which bind to the fluorescent protein, and/or the fluorescent protein. Preferably, the fluorescent protein is GFP.

In a preferred embodiment, the strain has been lyophilized. Lyophilization can be used to increase the stability and shelf-life of the strain.

In an eighth aspect, the present invention provides a pharmaceutical composition which comprises the modified strain in accordance with any of the previously disclosed embodiments and a pharmaceutically acceptable carrier or diluent and/or a pharmaceutically acceptable adjuvant.

In a preferred embodiment, the pharmaceutical composition comprises the modified *B. melitensis* 16M strain which has been further modified to express a fluorescent protein.

A pharmaceutical composition as described herein may also contain other substances. These substances include, but are not limited to, cryoprotectants, lyoprotectants, surfactants, bulking agents, anti-oxidants, and stabilizing agents. In some embodiments, the pharmaceutical composition may be lyophilized.

In one embodiment, a lyoprotectant is added to a pharmaceutical composition described herein. In some embodiments, a bulking agent is included in the pharmaceutical composition. Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition.

In a preferred embodiment, the pharmaceutical composition further comprises an adjuvant. Preferably, the adjuvant is selected from the list consisting of Alum, Freund's Incomplete Adjuvant, MF59®, synthetic analogs of dsRNA such as poly(I:C), bacterial LPSs, bacterial flagellin, imidazolquinolines, oligodeoxynucleotides containing specific CpG motifs, fragments of bacterial cell walls such as muramyl dipeptide and Quil-A®.

The pharmaceutical composition may be prepared for oral, sublingual, buccal, intravenous, intramuscular, subcutaneous, intraperitoneal, conjunctival, rectal, transdermal, topical and/or inhalation-mediated administration. In a preferred embodiment, the pharmaceutical composition may be a solution which is suitable for intravenous, intramuscular, conjunctival, transdermal, intraperitoneal and/or subcutaneous administration. In another embodiment, the pharmaceutical composition may be a solution which is suitable for sublingual, buccal and/or inhalation-mediated administration routes. In an alternative embodiment, the pharmaceutical composition may be an aerosol which is suitable for inhalation-mediated administration. In a preferred embodiment, the pharmaceutical composition may be prepared for subcutaneous and/or intraperitoneal administration.

The pharmaceutical composition may further comprise common excipients and carriers which are known in the state of the art. For solid pharmaceutical compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For solution for injection, the pharmaceutical composition may further comprise cryoprotectants, lyoprotectants, surfactants, bulking agents, anti-oxidants, stabilizing agents and pharmaceutically acceptable carriers. For aerosol administration, the pharmaceutical compositions are generally supplied in finely divided form along with a surfactant and propellant. The surfactant must, of course, be nontoxic, and is generally soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. For suppositories, traditional binders and carriers may include, for example, polyalkalene glycols or triglycerides.

In a preferred embodiment, the pharmaceutical composition is a vaccine capable of inducing an immune response. The design of pharmaceutical compositions for vaccines is well established, and is described, for example, in Remington's Pharmaceutical Sciences, latest edition, Mack Publishing Co., Easton, Pa., and in Plotkin and Orenstein's book entitled Vaccines, 4th Ed., Saunders, Philadelphia, Pa. (2004).

Medical Uses of the Modified 16M Strain

In a ninth aspect, the strain or pharmaceutical composition of the present invention can be used as a medicament. In a tenth aspect, the modified strain or pharmaceutical composition of the present invention can be used to treat and/or prevent brucellosis.

In a preferred embodiment, the infectious agent causing brucellosis is selected from the group consisting of *B. abortus, B. melitensis, B. suis, B. ovis, B. canis, B. neotomae, B. microti, B. ceti* and *B. pinnipedialis*. Preferably, the infectious agent causing brucellosis is selected from the group consisting of *B. abortus, B. melitensis* and *B. ovis*.

In a preferred embodiment, the strain or pharmaceutical composition is used to treat and/or prevent brucellosis in humans, cattle, goats, sheep, pigs, and/or dogs. Preferably, the strain or pharmaceutical composition is used to treat and/or prevent brucellosis in goats and/or sheep.

In a preferred embodiment, the individual or animal is inoculated with at least $10^4$ CFU (colony forming units) of the strain. Preferably, the individual or animal is inoculated with at least $10^5$, $10^6$, $10^7$, $10^8$, $10^9$, $10^{10}$ or $10^{11}$ CFU of the strain. More preferably, the individual or animal is inoculated with at least $10^9$ CFU of the strain. In an alternative embodiment, the individual or animal is inoculated with $10^4$ to $10^{12}$ CFU of the strain.

In a preferred embodiment, the strain or pharmaceutical composition is administered subcutaneously, intradermally, intravenously, intraperitoneally, by mucosae and/or conjunctively. Preferably, the strain or pharmaceutical composition is administered subcutaneously. In an alternative embodiment, the pharmaceutical composition is administered via a conjunctival administration.

In a preferred embodiment, the strain or pharmaceutical composition is used to prevent brucellosis. In this embodiment, the strain or pharmaceutical is administered as a prophylactic vaccine. Preferably, the strain or pharmaceutical composition is administered to an individual or animal who/which is at risk of becoming infected with bacteria of the genus *Brucella*.

In a preferred embodiment, the strain or pharmaceutical composition is used to treat brucellosis. In this embodiment, the strain or pharmaceutical is administered as a therapeutic vaccine. Preferably, the strain or pharmaceutical composition is administered to an individual or animal who/which suffers an infection from bacteria of the genus *Brucella*.

Kit Comprising the Modified 16M Strain

In an eleventh aspect, the present invention provides a kit comprising (i) a modified *B. melitensis* 16M strain wherein the wzm gene has been inactivated; and (ii) a pharmaceutically acceptable carrier or diluent.

The modified strain may be in accordance with any of the aforementioned embodiments outlined in this application. Further, the pharmaceutically acceptable carrier or diluent may be any of the aforementioned pharmaceutically acceptable carriers or diluents described in this application. In a preferred embodiment, the kit comprises instructions on how to combine the strain with the pharmaceutically acceptable carrier or diluent.

In a preferred embodiment, the modified strain is a lyophilisate. The lyophilisate may be contained in a separate container from the pharmaceutically acceptable carrier or diluent. Further, the kit may comprise instructions on how to combine the lyophilized strain with the pharmaceutically acceptable carrier or diluent.

In a preferred embodiment, the kit may further comprise an adjuvant. Preferably the adjuvant is selected from a list consisting of Alum, Freund's Incomplete Adjuvant, MF59, synthetic analogs of dsRNA such as poly(I:C), bacterial LPSs, bacterial flagellin, imidazolquinolines, oligodeoxynucleotides containing specific CpG motifs, fragments of bacterial cell walls such as muramyl dipeptide and Quil-A®.

In a preferred embodiment, the instructions included with the kit may also outline the administration of the strain to an individual or animal. The outline of the administration may include the dosage to be used, the frequency of administration and/or the administration route to be used.

In a twelfth aspect, the present invention provides the use of any of the described kits for the treatment and/or prevention of brucellosis. The use of the kit may be in line with any of the medical uses and methods of administration outlined in this application.

PCR-Multiplex Diagnostic Kit

In a thirteenth aspect, the present invention provides a kit for the identification of *Brucella* strains which comprise a partial or complete deletion of wzm. In a preferred embodiment, the kit comprises a forward and reverse primer which anneal to the regions flanking the wzm in the genome of a species of the genus *Brucella*. Preferably, the kit comprises SEQ ID NO: 2 as the forward primer and, SEQ ID NO: 3 and/or SEQ ID NO: 4 as the reverse primer(s). The primer sets may amplify an amplicon of about 1,573 bp (F1 and R4; AMP NO: 1) or about 724 bp (F1 and R5; AMP NO: 2) in Rev1 or 16M wild type strain; or a band of 931 bp (F1 and R4; AMP NO: 3) in the Δwzm mutants (Table 1). Since the identity between BMEI1415 and the corresponding orthologs in other *Brucella* species is at least 99.6%, this kit could be used to differentiate the wild type *Brucella* strains and *Brucella*Δwzm mutants.

EXAMPLES

Example 1

Culturing of *E. coli* and *Brucella* Strains

All strains were preserved in cryovials at −20° C., harvesting bacterial cultures in skimmed milk supplemented with 3% sterile lactose (Applichem Panreac) or with 20-40% glycerol (v/v).

To prepare suspensions with known concentration of *Brucella*, a preculture from a cryovial was prepared by growing bacteria onto a Blood Agar Base number 2 (Oxoid) plate, either plain (BAB) or supplemented with 5% Fetal Bovine Serum (Gibco) (BAB-S) for *B. ovis*. After incubation (3-5 days, at 37° C., and in atmosphere supplemented with 10% $CO_2$ for *B. ovis*) of this preculture, 2-3 colonies from BAB or BAB-S plates were transferred onto fresh BAB or BAB-S plates and incubated for 2 days as before. The grown colonies were harvested in sterile PBS pH 6.85 to obtain a concentrated suspension of bacteria, which was diluted in the same diluent up to obtain a suspension with around 0.170 units of absorbance at Optical Density of 600 nm adjusted by spectrophotometry. In our conditions, this suspension contains around $10^9$ CFU/mL. The exact number of bacteria was always determined retrospectively by serial dilutions in PBS, plating (100 μL by triplicate) and incubation of plates for 3-5 days at 37° C. The number of CFU/mL was calculated.

For the liquid culture of *Brucella*, 4-5 colonies of a BAB or BAB-S plate were inoculated into a trypticase soy broth (TSB, Pronadisa) and were incubated overnight at 37° C. and 150 rpm.

*E. coli* was cultured in Luria Bertani (LB, Pronadisa) broth or on LB agar plates. *E. coli* cultures were incubated at 37° C.

Appropriate concentrations of antibiotics were included in the agar plates and cultures for selection. All antibiotics were purchased from Sigma.

Example 2

Sequencing of the wzm Gene

The genome of Rev1 was extracted using the PureLink™ Microbiome DNA Purification Kit (Thermo Fisher Scientific). The wzm gene was amplified using primers F1 gcaaattgaaatggcagatg and R4 atgaaacgtggcgttagtcc (Table 1) and the PCR product was purified using a QIAquick PCR purification kit (Qiagen) and sequenced by Sanger method.

The resultant sequence is AMP NO: 1 (Table 1) including the SEQ ID NO: 1 described in the present application. This sequence in Rev1 is identical to that of the wzm gene in the *B. melitensis* 16M virulent strain (Genbank: CP007763.1) as well as 99.6% identity to that of *B. abortus* 2308 (Genbank: NC_007618) and vaccine S19 (Genbank: CP000887.1).

According to sequencing, the same allelic exchange plasmid can be used to partially delete wzm in both *B. melitensis* (16M and Rev1 strains) and *B. abortus* (2308 and S19 strains) species.

TABLE 1

Amplicon Numbers (AMP NO) used in this work and the correspondent DNA fragment size obtained by sequencing or by PCR with the indicated primer pairs with DNA from wild-type wzm or Δwzm genes.

| AMP NO: | DNA amplicon size | PCR primer pairs* | Primers nucleotide sequence (5'-3') |
|---|---|---|---|
| 1 | 1,573 bp (in wt) | F1/R4 | F1: gcaaattgaaatggca gatg (SEQ ID NO: 2) R4: atgaaacgtggcgtta gtcc (SEQ ID NO: 3) |
| 2 | 724 bp | F1/R5 | F1: gcaaattgaaatggca gatg (SEQ ID NO: 2) R5: gcgtgtaaattgcaag agga (SEQ ID NO: 4) |
| 3 | 931 bp (in Δwzm) | F1/R4 | F1: gcaaattgaaatggca gatg (SEQ ID NO: 2) R4: atgaaacgtggcgtta gtcc (SEQ ID NO: 3) |
| 4 | 484 bp | F1/R2 | F1: gcaaattgaaatggca gatg (SEQ ID NO: 2) R2: agcgcccacgtaaatc ag (SEQ ID NO: 5) |
| 5 | 465 bp | F3/R4 | F3: ctgatttacgtgggcg cttaacctgcgtggcagtag c (SEQ ID NO: 6) R4: atgaaacgtggcgtta gtcc (SEQ ID NO: 3) |
| 6 | 319 bp | F9/R5 | F9: atgatatcgtatatgg ctaatg (SEQ ID NO: 7) R5: gcgtgtaaattgcaag agga (SEQ ID NO: 4) |
| 7 | 816 bp | rrnBP1-F/Gfp_F-R2 | rrnBP1-F: gttgcgcggt cagaaaattatttta (SEQ ID NO: 8) Gfp_F-R2: ttatttgtat agttcatccatgcca (SEQ ID NO: 9) |

*F: forward; R: reverse.

Example 3

Cloning of Allelic Exchange Plasmids

All the *Brucella*Δwzm strains were constructed via a double recombination event using the allelic exchange plasmid pJQKm-Δwzm (FIG. 1). The primers required to construct the wzm truncated form (Δwzm) were designed using Primer3 on the basis of available sequence information of the *B. melitensis* 16M strain in the Kyoto Encyclopaedia of Genes and Genomes (KEGG) and the National Center for Biotechnology Information (NCBI).

The genome of *Brucella* strains was extracted and purified using a PureLink™ Microbiome DNA Purification Kit (Thermo Fisher Scientific). Alternatively, the DNA was extracted by re-suspending the bacteria in ultrapure water and boiling the suspension (100° C., 20 minutes) and then centrifuging (4,000 rpm, 10 minutes). DNA was recovered by collecting the supernatant.

To clone the allelic exchange plasmid for the partial deletion of wzm, a 484 bp fragment (AMP NO: 4, Table 1) was amplified using PCR with the primers F1 gcaaattgaaatggcagatg and R2 agcgcccacgtaaatcag (AMP NO: 3, Table 1). A 465 bp fragment (AMP NO: 5, Table 1) was amplified using PCR and primers F3 ctgatttacgtgggcgcttaacctgcgtggcagtagc and R4 atgaaacgtggcgttagtcc (Table 1). The two PCR products were combined by using overlap extension PCR and the full-length product was amplified using F1 gcaaattgaaatggcagatg and R4 atgaaacgtggcgttagtcc to produce the Δwzm cassette (FIG. 1). The Δwzm fragment had a deletion of 82% of the wzm wild-type gene (A80-721 from the total 783 bp of the wzm wild type). The Δwzm cassette was cloned into a pCR2.1 plasmid using the manufacturer's instructions (TOPO® TA Cloning®, Thermo Fisher Scientific).

The pJQKm suicide vector has been described previously (Scupham and Triplett, 1997. Gene, 202, 53-59). The pCR2.1Δwzm and pJQKm were digested using BamHI and XbaI and the Δwzm insert and pJQKm vector were gel extracted and purified. The Δwzm insert and pJQKm vector were ligated using a T4 DNA ligase resulting in the allelic exchange plasmid pJQKmΔwzm.

To insert gfp into the genome of the *B. melitensis* strains, the mini-Tn7 system was used by adaptation of the method described previously (Choi et al, 2005. Nature Methods, 2(6):443-8). The constitutive gfp expression was controlled by the rrnB P1 promoter contained in the fragment rrnB P1-gfp. The rrnB P1-gfp construct was extracted from the plasmid pUC18T-mini-Tn7-gfp-Gm$^r$ (GenBank: DQ493877.2). Thus, the rrnB P1-gfp fragment was amplified with the primers rrnBP1-F gttgcgcggtcagaaaattatttta and Gfp_F-R2 ttatttgtatagttcatccatgcca (AMP NO: 7) and cloned into a pCR2.1 plasmid using the manufacturer's instructions (TOPO® TA Cloning®, Thermo Fisher Scientific), and then subcloned into pUC18R6KT-mini-Tn7-Km$^r$ resistant to 50 μg/mL kanamycin (Km$^r$) (Llobet et al, 2009. Antimicrobial Agents and Chemotherapy, 53(1): 298-302) using EcoRI. This resulted in the plasmid pUC18R6KT-mini-Tn7-gfp (Table 1).

Example 4

Conjugation of *E. coli* with *Brucella* Strains and PCR Assessment of Mutants The pUC18R6KT-mini-Tn7-gfp or pJQKmΔwzm were transformed into *E. coli* S17 (λpir) and the plasmids were transferred into the receiving *Brucella* strains via conjugation. In the case of the partial deletion of wzm using the pJQKmΔwzm allelic exchange plasmid, 1 mL of overnight liquid culture of *B. melitensis* was cultured with 0.5 mL of overnight liquid cultures of *E. coli* S17 (λpir)-pJQKmΔwzm.

Figure 2:
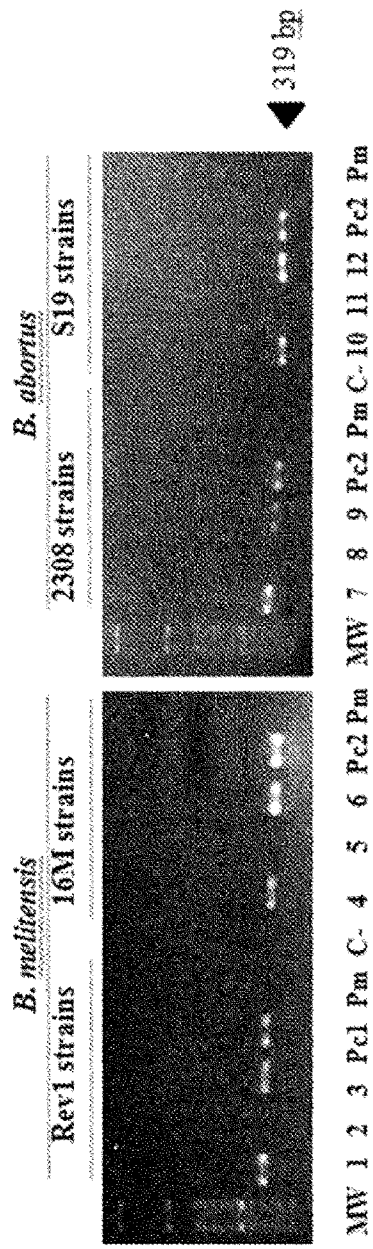
FIG. 2: Genetic assessment of *Brucella*Δwzm mutants and strains complemented with plasmids pSRK-wzm or pBBR-wzm. The presence (319 bp) or absence (no amplification) of the complete wzm gene was assessed by PCR with F9 and R5 (Table 1). MW: Molecular Weight marker; 1: Rev1 sibling; 2: Rev1Δwzm; 3: Rev1Δwzm-pSRK-wzm; Pc1: Plasmid for complementation pSRK-wzm; Pm: Plasmid for mutation pJQKm-Δwzm; C-: PCR negative Control; 4: 16M sibling; 5: 16MΔwzm; 6: 16MΔwzm-pBBR-wzm; Pc2: pBBR-wzm; 7: 2308 sibling; 8: 2308Δwzm; 9: 2308Δwzm-pBBR-wzm; 10: S19 sibling; 11: S19Δwzm; 12: S19Δwzm-pBBR-wzm.

For *Brucella*Δwzm strains, the selection of transconjugants after the first recombination (integration of the suicide vector in the chromosome) was selected by growing the bacteria in BAB supplemented with 50 μg/mL kanamycin (Km$^r$) and susceptibility to 5% sucrose (Sac$^s$). The second recombination (excision of the mutator plasmid and leading to construction of the mutant strain by allelic exchange) was selected by sucrose resistance and kanamycin sensitivity (FIG. 1). Finally, the resulting colonies were screened by two PCR, i.e., one PCR with primers F1 gcaaattgaaatggcagatg and R4 atgaaacgtggcgttagtcc which amplified a fragment of 931 bp in the Δwzm mutants and a fragment of 1,573 bp in the parental strain (Table 1) and other PCR with F9 atgatatcgtatatggctaatg and R5 gcgtgtaaattgcaagagga amplifying a 319 bp PCR product in the wild type and sibling strains (FIG. 2). For PCR, genomic DNA was extracted by re-suspending the bacteria in ultrapure water and boiling the suspension at 100° C. for 20 minutes and then centrifuging the resultant liquid at 4,000 rpm for 10 minutes and collecting the supernatant.

In all cases, three clones of each mutant and one sibling strain (i.e., submitted to the same subcultures than the correspondent mutant; FIG. 1) as control were used in most of experiments, to assess the absence of uncontrolled changes during the genetic manipulations.

A Rev1 strain containing the partial deletion (82%) of the wzm gene was identified and called Rev1Δwzm. This strain was also deposited at a depository in accordance with the Budapest Treaty.

*Brucella*Δwzm mutants were complemented by conjugation with the donor *E. coli* S17pBBR-wzm or *E. coli* S17pSRK-wzm. The complemented strains were selected on BAB plates supplemented with 20 μg/mL of chloramphenicol (BAB-Cm$_{20}$) or 50 μg/mL of kanamycin (BAB-Km$_{50}$) allowing the selection of conjugants carrying the non-integrative plasmid pBBR-wzm or pSRKwzm, respectively. Transconjugants were checked by PCR (FIG. 2) with F9 atgatatcgtatatggctaatg and R5 gcgtgtaaattgcaagagga primers (Table 1), amplifying DNA fragments of 319 bp (AMP NO: 6) exclusively in strains carrying the wild type wzm gene (parental and sibling strains) or the pBBR-wzm or pSRK-wzm complementation plasmids (FIG. 2).

Example 5

Phenotypic Characterization of the *Brucella*Δwzm Mutants

The selected clones of Δwzm mutants were analyzed by the classical markers for *Brucella* typing following the standard protocols (Alton et al., 1988. Techniques for the Brucellosis. Laboratory Paris: INRA) of crystal violet-oxalate exclusion, catalase, oxidase, urease and acriflavine tests (all from Sigma Aldrich), sensitivity to Tb, Wb, Iz and R/C phages, agglutination with anti-A and anti-M monospecific sera, both $CO_2$- and serum-dependence, susceptibility to dyes (i.e., thionine blue 10, 20 and 40 μg/mL, fuchsine 10 and 20 μg/mL, and safranin 100 μg/mL; Sigma) and to the antibiotics penicillin 5 mg/mL ($P_5$) and streptomycin 2.5 μg/mL ($Str_{2.5}$), as shown in Table 2.

Figure 3:
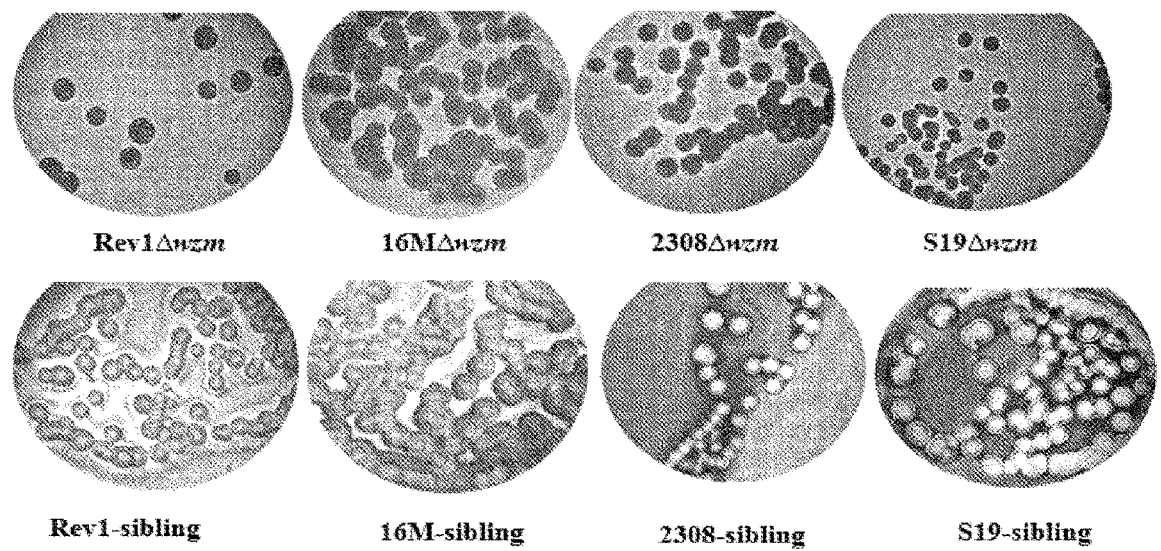
FIG. 3: *Brucella*Δwzm mutants (upper panels) showed a rough phenotype by crystal violet-oxalate staining, in contrast to the sibling strains (lower panels).

Moreover, Rev1Δwzm, 16MΔwzm, 2308Δwzm and S19Δwzm strains showed a R-LPS phenotype, regarding positive staining with crystal violet-oxalate technique (FIG. 3).

Figure 4:
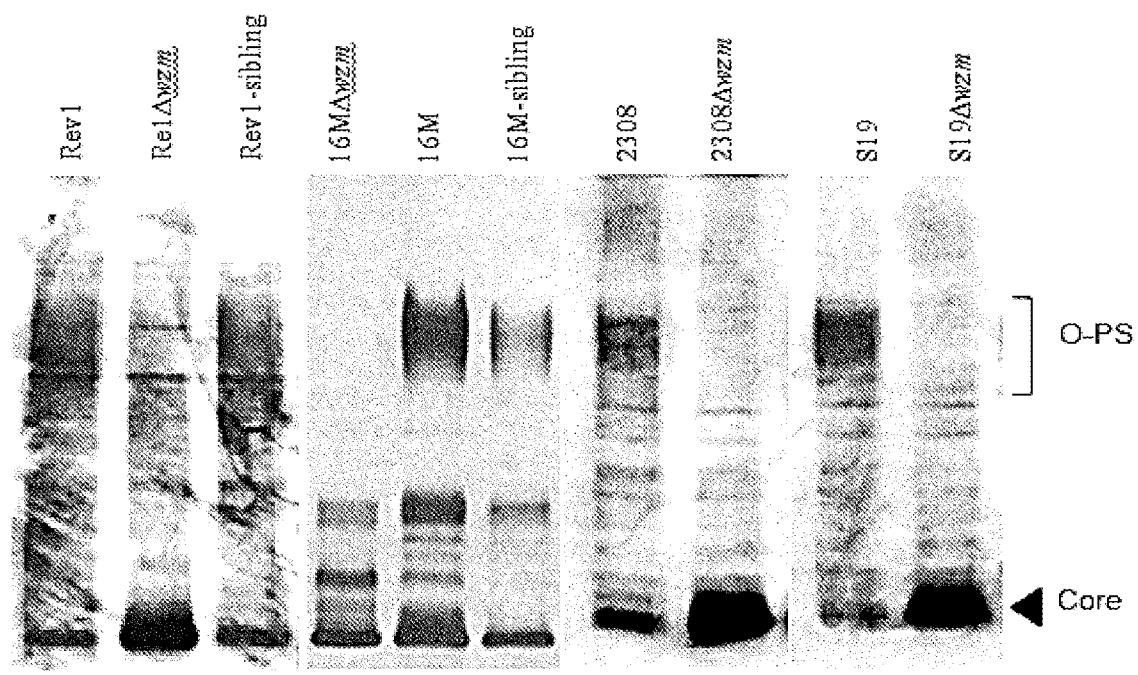
FIG. 4: *Brucella*Δwzm mutants have R-LPS with an intact core and synthesize free O-PS that accumulates inside the bacteria. Complementation of these *B. melitensis* and *B. abortus* Δwzm strains with plasmids pSRK-wzm or pBBR-wzm restores the S-LPS phenotype. Representative images of (A) LPS silver staining of Rev1Δwzm, 16MΔwzm, 2308Δwzm and S19Δwzm. (B) Western Blot with sera recognizing O-PS epitopes M in Rev1Δwzm, C in 16MΔwzm, or A in both 2308Δwzm and S19Δwzm; 1: Rev1 sibling; 2: Rev1Δwzm; 3: Rev1Δwzm-pSRK-wzm; 4: 16M sibling; 5: 16MΔwzm; 6: 2308 sibling; 7: 2308Δwzm; 8: 2308Δwzm-pBBR-wzm; 9: S19 sibling; 10: S19Δwzm; 11: S19Δwzm-pBBR-wzm. (C) Immunofluorescence and epifluorescence microscopy of 16MΔwzm::gfp-pBBR-wzm, 16MΔwzm::gfp, and 16M sibling, using a primary MoAb anti-C O-PS epitope and a secondary antibody labelled with Texas Red.
Figure 4:
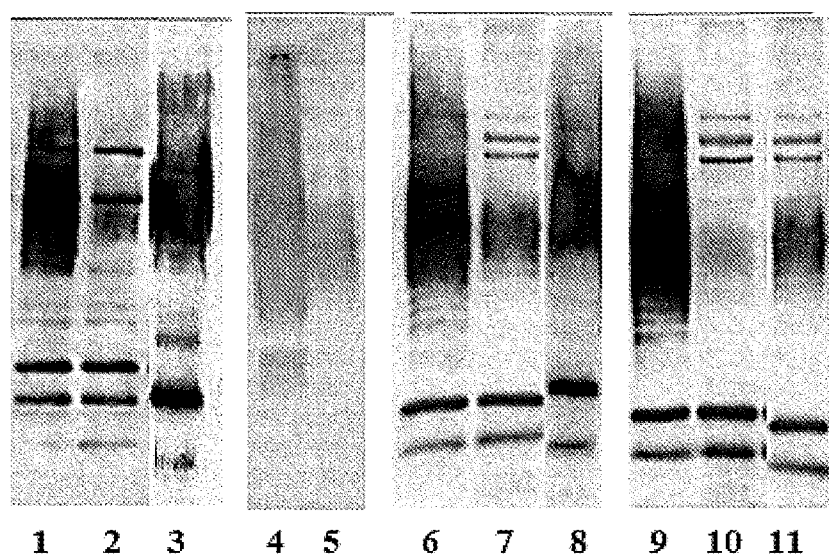
Figure 4:
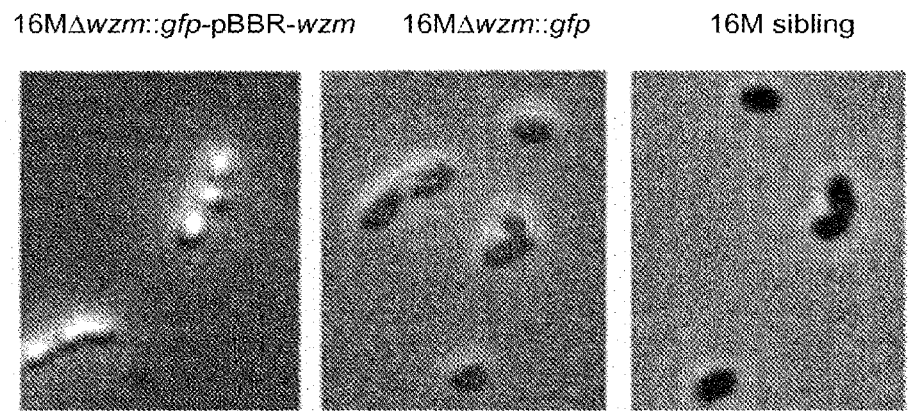

Also, the LPS structure of all Δwzm mutants and complemented strains was studied by SDS-PAGE and silver staining modified for LPS. As shown in FIG. 4A, both Rev1Δwzm, 16MΔwzm, 2308Δwzm and S19Δwzm mutants showed a R-LPS with an intact core identical to that of the parental and/or sibling strains. However, when analyzed antigenically by Western Blot using anti-M, anti-C or anti-A O-PS epitopes, all Δwzm mutants showed O-PS in lower amounts or antigenically different epitopes (Cloeckaert et al., J Gen Microbiol. 1992 June; 138(6):1211-9) to those present in the O-PS of the S-LPS (FIG. 4B). Moreover, 16MΔwzm::gfp-pBBR-wzm complementation was assessed by epifluorescence microscopy, by using a primary MoAb (Monoclonal Antibody) anti-C O-PS epitope and a secondary antibody labelled with Texas Red. 16MΔwzm::gfp and 16M sibling strains were used as controls (FIG. 4C).

Besides PCR assessment (see Example 4, FIG. 2), the phenotypic characterization showed that the complemented strains restored the S-LPS phenotype (FIGS. 3, 4B and 4C).

Example 7

The Growth of 16MΔwzm but not Rev1Δwzm is Inhibited by the Presence of 10% $CO_2$ in the Atmosphere of Incubation. This Defect is Restored by Growing in Agar Supplemented with Bovine Foetal Sera Bacterial growth of Δwzm mutants were studied in BAB plates incubated in normal atmosphere or supplemented with 10% $CO_2$. For this, 100 µL of bacterial suspensions containing ≈5×10² CFU/mL were plated in triplicate, and the number of CFU/100 µL determined after incubation (3-5 days, 37° C.). Moreover, 16MΔwzm was analyzed to deter-

TABLE 2

Phenotypic characterization of Rev1Δwzm, 16MΔwzm, 230SΔwzm and S19Δwzm

| STRAIN | Phage lysis | | | | $CO_2$ dependent | Catalse/ Oxidase/ Urease | Acriflavine and crystal violet staining | Agglutination with Sera anti- | | Growth in dyes in BAB-S presence/absence of $CO_2$ | | | | | |
|---|---|---|---|---|---|---|---|---|---|---|---|---|---|---|---|
| | Tb | Wb | Iz | R/C | | | | A | M | Thionine 10 | 20 | 40 | Basic fuchsine 10 | 20 | Safranin 100 |
| 16M | — | — | -2 | — | — | +/+/+ | -/- | — | + | +/+ | +/- | -/- | +/+ | +/+ | +/+ |
| 16MΔwzm | — | — | — | -3 | — | +/+/+ | +/+ | — | — | +/+ | +/- | -/- | +/+ | +/+ | +/- |
| Rev1 | — | — | 0 | — | — | +/+/+ | -/- | — | + | +/+ | +/- | -/- | +/+ | +/- | +/- |
| Rev1Δwzm | — | — | — | -4 | — | +/+/+ | +/+ | — | — | +/+ | -/- | -/- | +/+ | +/+ | -/- |
| 2308 | -3 | -4 | -4 | — | — | +/+/+ | -/- | + | — | -/- | -/- | -/- | +/+ | +/+ | +/+ |
| 2308Δwzm | ND | ND | ND | ND | — | +/+/+ | +/+ | — | — | -/- | -/- | -/- | -/- | +/+ | +/+ |
| S19 | -3 | -3 | -2 | — | — | +/+/+ | -/- | + | — | -/- | -/- | -/- | +/+ | +/+ | +/+ |
| S19Δwzm | — | — | — | -3 | — | +/+/+ | +/+ | — | — | -/- | -/- | -/- | +/+ | +/+ | +/+ |

ND: Not Determined

Example 6

Deletion of wzm in Rev1Δwzm and 16MΔwzm is Stable After Subcultures In Vitro and In Vivo in Mice BrucellaΔwzm mutants were subcultured for 20 consecutive passages in BAB plates by transferring colonies onto fresh plates every 3-4 days, after the plates were incubated at 37° C. Besides analysis of these cultures, the grown bacteria were kept for 2 months at 4° C. to assess their stability after storage. Moreover, representative number of CFU isolated from mice spleens in the experiments described in Examples 12 and 13 were selected for stability assessment.

Each selected culture was analyzed for the presence of the deletion by PCR with primers F1 gcaaattgaaatggcagatg and R4 atgaaacgtggcgttagtcc, allowing DNA amplification in both wt and Δwzm bacteria (Table 1), and by phenotypic analysis, i.e., colony size after incubation at 37° C. and crystal violet-oxalate staining. Finally, inocula containing 2×10³ CFU/mL were adjusted by spectrophotometry and plated in triplicate (3×100 µL) in five plates, in order to analyses the colony size after 5 days of incubation at 37° C. and colony phase by crystal violet staining in around 3,000 CFU.

All the colonies analyzed showed the expected genotype and phenotype, indicating that the genetic modification is stable.

mine the frequency of inhibition (i.e., the number of CFU/mL isolated after $CO_2$ incubation with respect to the number of CFU/mL isolated after incubation in normal atmosphere) by seeding all the bacterial dilutions prepared in both BAB and BAB-S. Each counting was repeated three times. Results are presented as mean±standard deviation (n=9) of individual counts. Statistical comparisons of means were performed by a one-way ANOVA and PLSD tests.

As shown in Table 3, 16MΔwzm but not Rev1Δwzm was unable to growth in BAB under $CO_2$ incubation conditions.

TABLE 3

Growth in BAB plates incubated in normal atmosphere or supplemented with 10% $CO_2$. Number of CFU/100 µL of bacterial suspensions containing ≈5 × 10² CFU/mL. Mean and standard deviation of three experiments by triplicate plating of 100 µL in BAB.

| | No. CFU/100 µL (mean ± SD) | |
|---|---|---|
| Strain | Normal atmosphere | 10% $CO_2$ |
| Rev1 | 70.1 ± 5.4 | 62.9 ± 8.3 |
| Rev1-sibling | 53.8 ± 3.0 | 61.8 ± 4.5 |
| Rev1Δwzm | 42.3 ± 2.3 | 28.6 ± 4.2 |
| Rev1Δwzm::gfp | 37.7 ± 2.4 | 21.5 ± 1.3 |
| 16M | 57.9 ± 2.8 | 67.8 ± 2.5 |
| 16M-sibling | 50.5 ± 1.8 | 73.1 ± 3.1 |
| 16MΔwzm | 31.7 ± 3.5 | 0 [a] |
| 16MΔwzm::gfp | 21.4 ± 1.5 | 0 [a] |

[a] PLSD tests: p < 0.0001 vs. normal atmosphere and vs. 16M and Rev1 sibling strains The frequency of inhibition of 16MΔwzm after incubation of BAB plates in $CO_2$-atmosphere was of 1-0.39×10⁻² CFU/mL. This phenotype did not occur when 16MΔwzm was cultured in BAB-S plates (Table 4).

TABLE 4

Inhibition frequency of 16MΔwzm and 16MΔwzm::gfp in BAB and BAB-S plates incubated in atmosphere normal or supplemented with a 10% $CO_2$.

| Strain | CFU/mL | |
|---|---|---|
| | Normal atmosphere | 10% $CO_2$ (Inhibition frequency) |
| 16M | | |
| BAB | $4.3 \times 10^8$ | $4.2 \times 10^8$ ($1 \times 10^0$) |
| BAB-S | $4.9 \times 10^8$ | $4.2 \times 10^8$ ($1 \times 10^0$) |
| 16M sibling | | |
| BAB | $5.4 \times 10^8$ | $6.2 \times 10^8$ ($1 \times 10^0$) |
| BAB-S | $6.6 \times 10^8$ | $6.2 \times 10^8$ ($0.9 \times 10^0$) |
| 16MΔwzm | | |
| BAB | $4.3 \times 10^8$ | $4.4 \times 10^6$ ($1 \times 10^{-2}$) |
| BAB-S | $3.4 \times 10^8$ | $4.5 \times 10^8$ ($1 \times 10^0$) |
| 16MΔwzm::gfp | | |
| BAB | $4.1 \times 10^8$ | $1.6 \times 10^6$ ($0.39 \times 10^{-2}$) |
| BAB-S | $3.9 \times 10^8$ | $4.5 \times 10^8$ ($1 \times 10^0$) |

Example 8

Rev1Δwzm is More Susceptible to Streptomycin than Rev1

In contrast to other *Brucella* species such as *B. melitensis* 16M, and *B. abortus* 2308 and S19, Rev1 presents a relative resistance to 2.5 μg/mL of streptomycin ($Str_{2.5}$) when incubated in normal atmosphere (in 10% $CO_2$ all the *B. melitensis* strains show similar resistance). This relative resistance to $Str_{2.5}$ in vitro is directly related to the inefficiency of streptomycin-based treatments (an antibiotic of choice in humans) against Rev1 infections in both humans and in animal models (Grilló et al. 2006. J Antimc Chemother. 58 (3):622-626).

To assess this property in Rev1Δwzm, bacterial suspensions containing ≈$2 \times 10^3$ CFU/mL were prepared in PBS and cultured by plating 100 μL in triplicate in BAB and BAB supplemented with $Str_{2.5}$ (BAB-$Str_{2.5}$). The Rev1 sibling strain was used as control. Plates were incubated at 37° C., for 5 days, in normal atmosphere and the mean±standard deviation (n=3) number of CFU/mL was determined. The experiment was repeated three times. Statistical comparisons of means were performed by ANOVA and PLSD tests.

Figure 5:
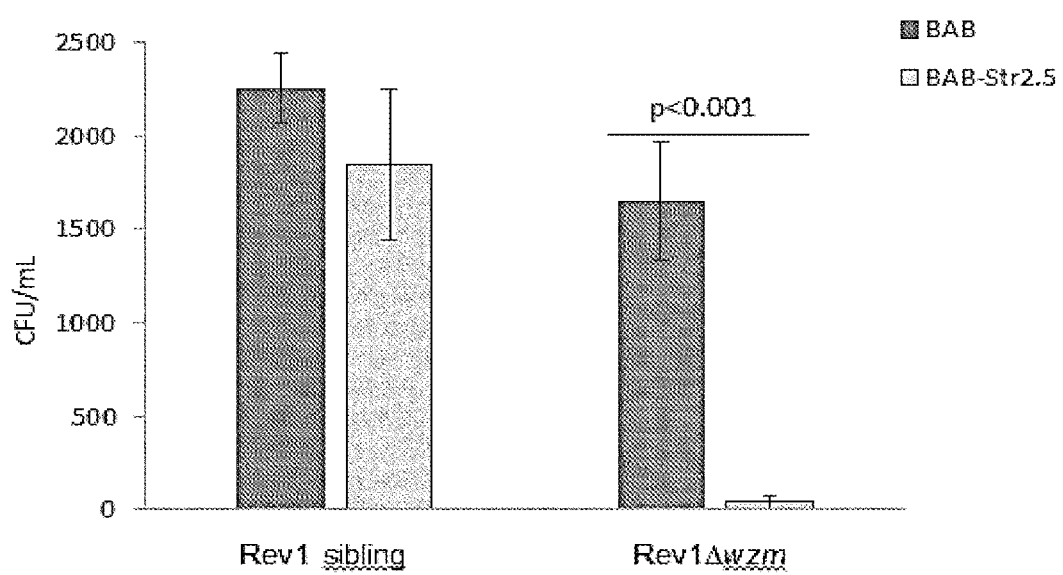
FIG. 5: Rev1Δwzm is more susceptible to streptomycin than Rev1. Exponentially growing bacteria were adjusted to ≈$2\times10^3$ CFU/mL in sterile PBS and 100 μL by triplicate were plated in BAB and BAB supplemented with 2.5 μg/mL of streptomycin (BAB-$Str_{2.5}$). Rev1 sibling strain (Rev1) was used as control. After 5 days of incubation at 37° C., the number of CFU/mL was calculated. Data points represent the mean±standard deviation (n=3). The results are representative of three independent experiments. Statistical comparisons of means were performed by ANOVA and PLSD tests.

As result, Rev1Δwzm was more (p<0.001) susceptible to $Str_{2.5}$ than Rev1 sibling (FIG. 5).

Example 9

16Δwzm is More Susceptible to Desiccation than 16M, and Rev1Δwzm is as Susceptible as Rev1

Desiccation resistance Rev1Δwzm, 16MΔwzm, Rev1 and 16M was tested by aliquoting 200 μL/well of a ≈$10^9$ CFU/mL suspension in TSB in 12-well polystyrene plates. The suspensions were allowed to dry at room temperature in the dark for 6 days. Then, the pellet was rehydrated in PBS, serially diluted, and plated on BAB plates in order to determine the number and percentage of surviving bacteria.

Figure 6:
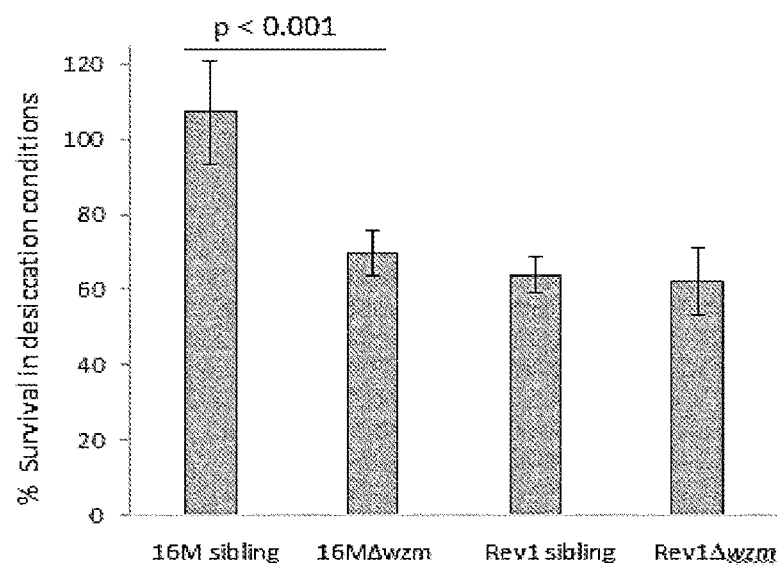
FIG. 6: 16MΔwzm is more susceptible to desiccation than 16M, but not Rev1Δwzm with respect to Rev1. Suspensions containing ≈$10^9$ CFU/mL of 16MΔwzm, 16M, Rev1Δwzm or Rev1 were allowed to dry in 12-well polystyrene plates and then maintained at room temperature under dark conditions. The number of viable cells was quantified after rehydration of the dried pellet in PBS, and the percentage of surviving bacteria was determined six days later. Data points represent the mean±standard deviation (n=3). Statistical comparisons of means were performed by ANOVA and PLSD tests.

As can be seen in FIG. 6, the partial deletion of the wzm gene in 16MΔwzm further decreased (p<0.001) the 16M sibling strain's ability to survive in dry environments. However, Rev1Δwzm is as susceptible as Rev1 sibling. These findings provide evidence that the 16MΔwzm would be less likely to persist in the environment than the 16M virulent strain.

Example 10

Rev1Δwzm is More Susceptible than 16MΔwzm to the Bactericidal Cationic Peptides of the Innate Immune System. Both Δwzm Mutants are More Susceptible than Parental or Sibling Strains Polymyxin B was used as model of bacterial susceptibility to cationic peptides of the innate immune system. For this, exponentially growing Rev1Δwzm or 16MΔwzm were adjusted to $2-3 \times 10^3$ CFU/mL in PBS and mixed with different concentrations from 3 to 0.188 mg/mL Polymyxin B in Phosphate Saline Acid buffer (PSA; 0.133M NaCl, 0.1M; $NaH_2PO_4$, pH 4.6) in 24-well microtiter plates in duplicate. Suspensions (100 μL, in triplicate) were plated in BAB and the number of viable CFU was recorded after incubation for 1 h at 37° C. Both parental and sibling strains were used as controls. Data points represent the mean±standard deviation (n=3) of CFU/mL.

Figure 7:
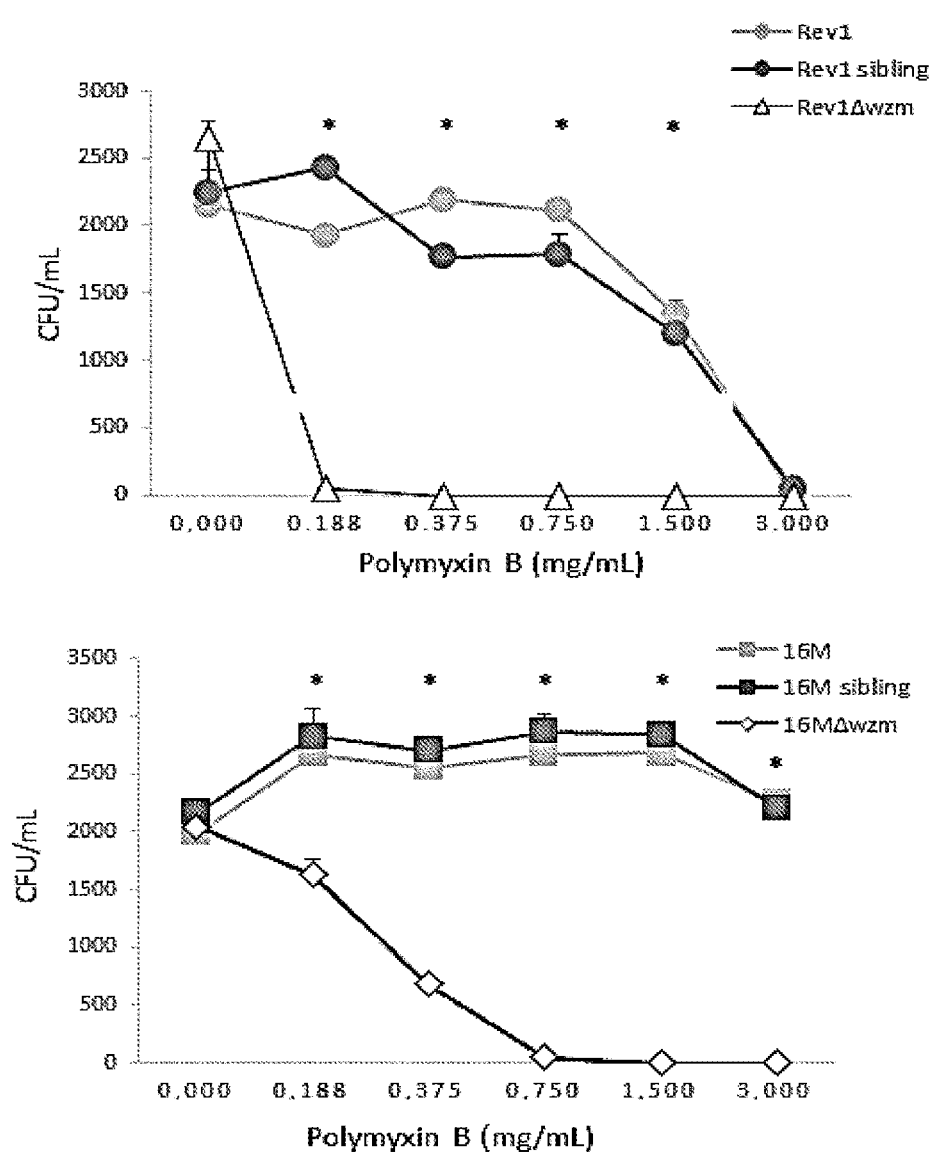
FIG. 7: Rev1Δwzm is more susceptible to Polymyxin B than 16MΔwzm, and Rev1 and 16M parental and sibling strains, as a model of susceptibility to the cationic peptides of the innate immune system. Cultures with 2-$3\times10^3$ CFU/mL in PBS were incubated (1 h, 37° C.) with different concentrations of Polymyxin B prepared in PSA and the number of viable cells was then quantified by plating in BAB and incubating the plates (5 days, 37° C.). Data points represent the mean±standard deviation (n=3) of CFU/mL at each Polymyxin B concentration. Statistical comparisons of means were performed by ANOVA and PLSD tests: *$p<0.0001$.
Figure 9:
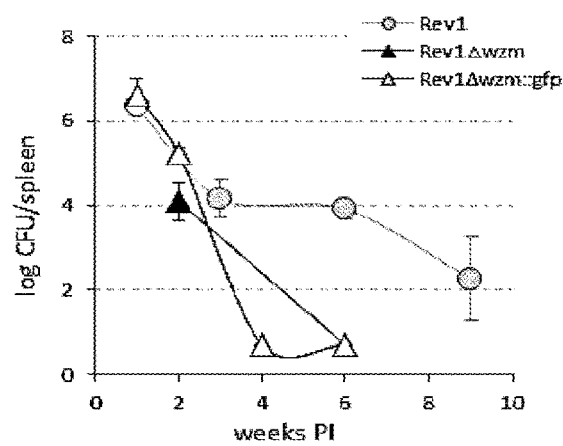
FIG. 9: Rev1Δwzm is more attenuated in BALB/c mice than other *Brucella*Δwzm mutants and induced a peak of transient splenomegaly, usually associated with an effective immunogenic potency. Panels represent the bacterial burden in spleens and spleen weights in BALB/c mice intraperitoneally inoculated with (A-B) Rev1Δwzm and Rev1Δwzm::gnfp vs. Rev1 parental strain; (C-D) 16MΔwzm and 16MΔwzm::gfp vs. 16M parental strain; (E-F) 2308Δwzm vs. 2308 parental strain; and (G-H) S19Δwzm vs. S19 strain. The Δwzm mutants were injected at doses of $10^8$ CFU/mouse, and the S-LPS strains, at $10^6$ CFU/mouse. Results are expressed as the mean±standard deviation (n=5) of the log CFU/spleen or weight grams/spleen at each selected time point. Similar results were obtained with the corresponding *Brucella*::Tn7-gfp tagged strains, indicating that gfp tagging does not affect the biological properties of *Brucella*.
Figure 9:
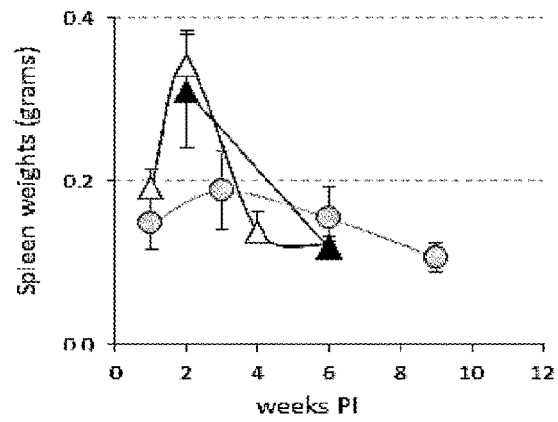
Figure 9:
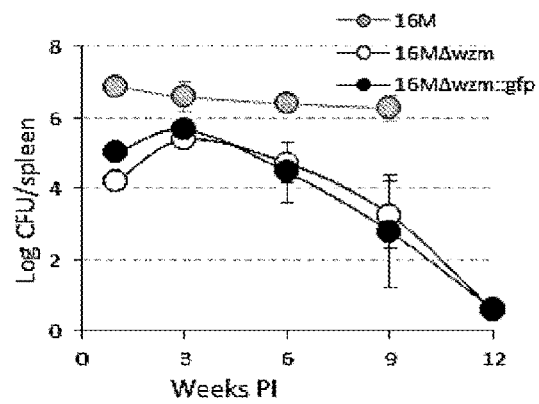
Figure 9:
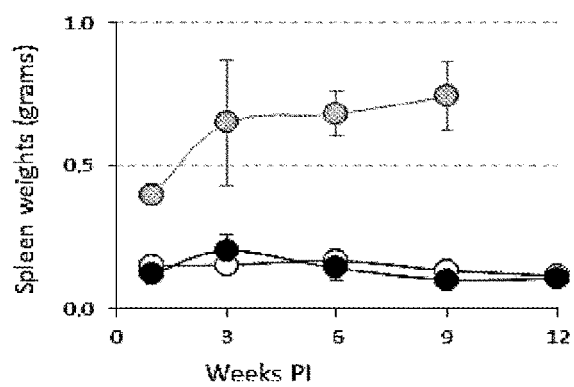
Figure 9:
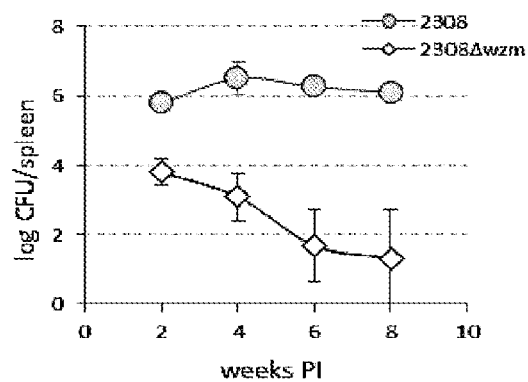
Figure 9:
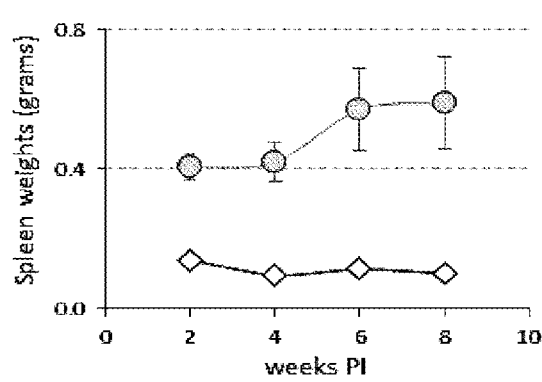
Figure 9:
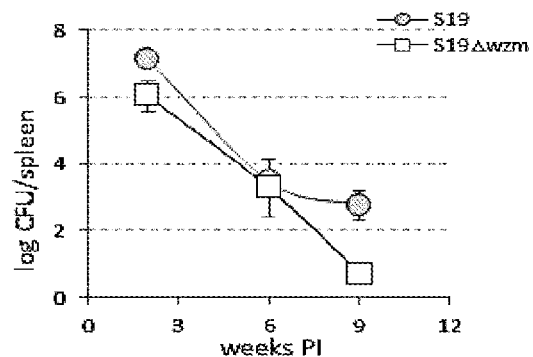
Figure 9:
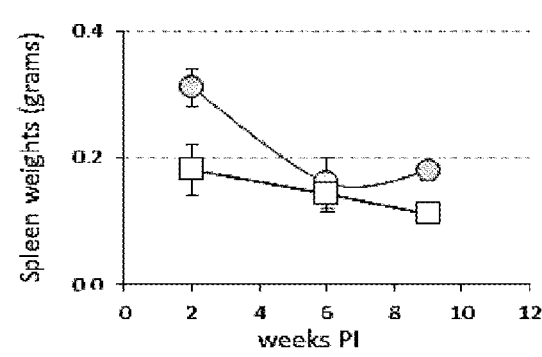

FIG. 7 shows that Rev1Δwzm strain is more susceptible than 16MΔwzm to the detrimental effects of Polymyxin B. Moreover, both Δwzm mutants were far more susceptible than Rev1 and 16M parental and sibling strains. In fact, Rev1Δwzm failed to grow after incubation in the presence of the lowest concentration tested (0.188 mg/mL) while 16MΔwzm was not totally inhibited up to a Polymyxin B concentration of 0.750 mg/mL, under the same experimental conditions (FIG. 7). In contrast, Rev1 parental and sibling strains were inhibited at 3 mg/mL, while the virulent 16M resisted even at this high concentration. These results are in concordance with the different in vivo persistence of Rev1Δwzm and 16MΔwzm observed in mice (FIG. 9).

Example 11

Rev1Δwzm and 16MΔwzm are More Susceptible Than Rev1 and 16M Parental Strains to Conventional Sheep and Cattle Sera Bacteria in exponential phase were adjusted to a concentration of ≈$10^4$ CFU/mL in PBS and dispensed in microtiter plates (45 μL/well) by mixing with either normal or decomplemented (1 hour, 56° C.) ovine or bovine sera (90 μL/well). After incubation (18 h, 37° C.), 65 μL of TSB was dispensed into each well, the bacterial suspension mixed, 50 μL/well was plated onto BAB, and plates were incubated (5 days, 37° C.) to determine the number of CFU/mL and the percentage of bacterial survival. A *B. melitensis* mutant with minimal core was used as positive control (C+) of high susceptibility to normal serum. Results are expressed as the mean±standard deviation (n=3) of survival percentage. Statistical comparisons of means were performed by ANOVA and PLSD tests.

Figure 8:
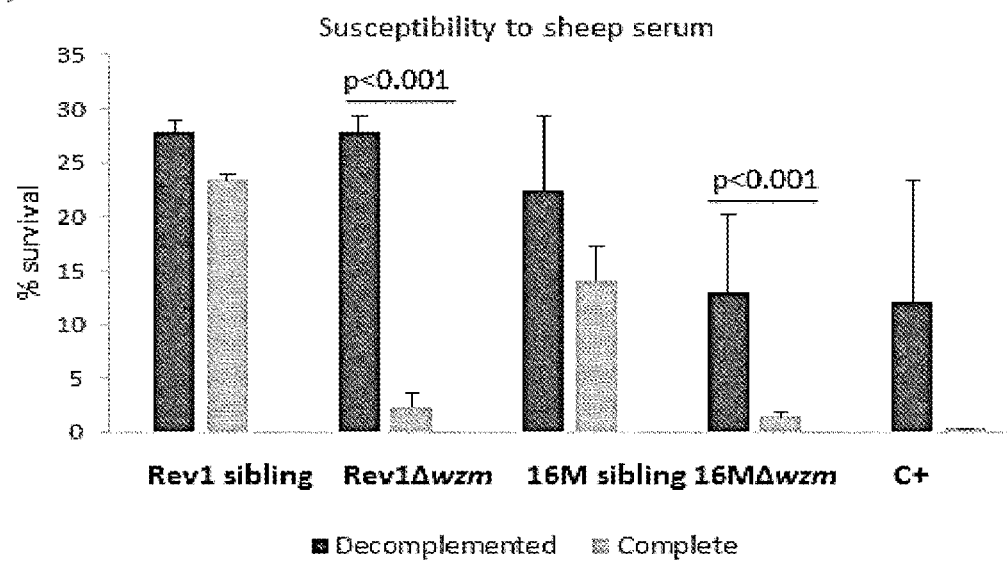
FIG. 8: Rev1Δwzm and 16MΔwzm are more susceptible than Rev1 and 16M parental strains to conventional sheep and cattle sera, mainly due to the effect of the serum complement. Bacterial cultures containing $10^4$ CFU/mL in PBS were mixed with normal or decomplemented (heat inactivated 56° C., 1 h) sera from sheep (A) or cows (B). After incubation (18 h, 37° C.), each suspension was plated onto BAB and plates were incubated (5 days, 37° C.) to determine the number of CFU/mL and the percentage of bacterial survival. A *B. melitensis* mutant with minimal core (C+) was used as a control of susceptibility to normal serum. Results are expressed as the mean±standard deviation (n=3) of survival percentage. Statistical comparisons of means were performed by ANOVA and PLSD tests.
Figure 8:
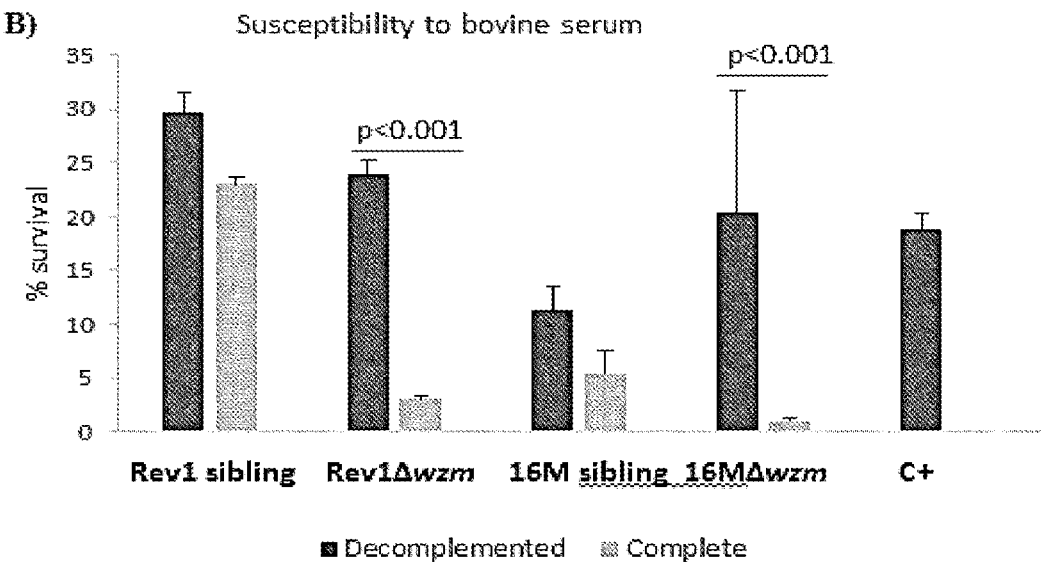

As can be seen in FIG. 8, the Rev1Δwzm and 16MΔwzm strains are more susceptible than the Rev1 or 16M parental strains to the bactericidal effect of both sheep and cow normal serum.

Example 12

Rev1Δwzm is More Attenuated Than 16MΔwzm in Balb/C Mice

Female BALB/c mice of 7 weeks of age (Charles River Laboratories, Barcelona, Spain) were housed in the animal building of the Instituto de Agrobiotecnologia (registration number ES/31-2016-000002-CR-SU-US) with water and food ad libitum. Animals were randomly allotted and acclimated for 1-2 weeks before the start of the experiments. Animal handling and experimental procedures were in accordance with European (DOCE 86/609/EEC), National (RD 1201/2005) and Regional (Ley 11/2003) directives, and were supervised by the Ethical Committee of the Institution.

Mice were inoculated intraperitoneally with ≈$10^8$ CFU/mouse of Rev1Δwzm, Rev1Δwzm::gfp, 16MΔwzm or 16MΔwzm::gfp (R-LPS strains) and $10^6$ CFU/mouse of Rev1 or 16M sibling strains (S-LPS strains). Additional groups of mice inoculated with ≈$10^8$ CFU/mouse of S19Δwzm or 2308Δwzm B. abortus mutants and with $10^6$ CFU/mouse of S19 or 2308 sibling strains were used to compare the effect of this mutation in different Brucellae backgrounds. At selected intervals, groups of 5 mice were necropsied to determine the number of viable bacteria present in the spleens as well as the spleens weights, as previously reported (Grilló et al., 2012. Veterinary Research, 43 (1): 29). Viable bacteria were identified on BAB plates. The rough identity of the spleen isolates was confirmed by the crystal violet-oxalate staining method as well as by PCR. Results were expressed as the mean±standard deviation (n=5) of individual log CFU/spleen or grams/spleen. Statistical comparison of means was performed by a one-way ANOVA followed by the Fisher Protected Least Significant Differences (PLSD) tests.

As can be seen in FIGS. 9A and 9C, the partial deletion of the wzm gene led to a decrease in the number of B. melitensis present in the mice spleens in comparison to the correspondent Rev1 or 16M sibling strains. However, Rev1Δwzm was much more attenuated than 16MΔwzm, since complete clearance of infections from spleens occurred before week 4 or week 12 for Rev1Δwzm or 16MΔwzm, respectively. In contrast to B. melitensis, both B. abortus 2308Δwzm and S19Δwzm mutants persisted in the spleens similarly, i.e., somewhat more than 8 weeks or less than 9 weeks, respectively (FIGS. 9E and 9G). These findings indicated that both B. abortus mutants were more attenuated than the 16MΔwzm mutant but less than Rev1Δwzm.

Unexpectedly, the higher attenuation of Rev1Δwzm was accompanied by the induction of a transient splenomegaly that peaked at week 2 post-infection (FIG. 9B). This finding is generally associated with the triggering of an effective immune-response (Conde-Álvarez et al. 2012. PLoS Pathog. 8(5): e1002675). This splenic reaction was not observed in 16MΔwzm (FIG. 9D) neither in B. abortus 2308Δwzm and S19Δwzm mutants (FIGS. 9F and 9H).

The Rev1Δwzm::fp and 16MΔwzm::gfp strains showed similar virulence and splenomegaly than Rev1Δwzm and 16MΔwzm, respectively (FIGS. 9A-9D), indicating that the insertion of the mini-Tn7-gfp in the genome did not affect the biological properties of Rev1Δwzm and 16MΔwzm.

Example 13

Rev1Δwzm Does Not Infect Placentas or Foetuses of Pregnant Mice

CD1 female mice (n=7) at 4.5 days of pregnancy were intraperitoneally infected with ≈$7×10^6$ CFU/mouse of Rev1Δwzm or 16MΔwzm or with $7×10^5$ CFU/mouse of Rev1 or 16M. All mice were sacrificed at term pregnancy to assess macroscopic lesions at necropsy as well as bacteriology of spleen, placenta and foetus samples. The number of viable bacteria (log CFU/organ) in each tissue was determined by plating on BAB. Moreover, the number of pregnant females, the infected placentas, and the dams carrying infected foetuses were recorded.

As can be seen in Table 5, all mice showed well-established infections in spleens at similar levels (4-5 logs) between groups. However, the splenomegaly generated by Rev1Δwzm and 16MΔwzm in pregnant dams were moderate or low, respectively, in contrast to Rev1 and 16M parental strains (Table 5). Surprisingly, Rev1 (and to less extend 16M) induced higher splenomegaly in pregnant (Table 5) than in non-pregnant mice at week 2 (FIG. 9). However, Rev1Δwzm and 16MΔwzm mutants induced similar splenomegaly in pregnant and non-pregnant mice, showing higher spleen weights at week 2 in Rev1Δwzm than in 16MΔwzm (0.30 vs 0.16 grams/spleen, Table 5). Full term pregnancies were observed in most of the mice vaccinated with Rev1Δwzm or 16MΔwzm, as well as in those vaccinated with Rev1, but only few dams infected with 16M parental achieved full-term pregnancy. Moreover, while Rev1Δwzm and 16MΔwzm were practically unable to colonize the placentas and foetuses at the dose administered, infection with one logarithm less of Rev1 allowed colonization of these tissues at very high levels (6-8 logs of infection) in all dams (Table 5).

Figure 10:
FIG. 10: Rev1Δwzm and 16MΔwzm (right panel) do not induce placental macroscopic lesions, in contrast to Rev1 or 16M parental or sibling strains (left panel). Arrows indicate macroscopic lesions in individual placentas, in contrast to healthy placentas in Rev1Δwzm or 16MΔwzm.
Figure 10:
Figure 10:
Figure 10:

These levels of infection were accompanied by macroscopic lesions in Rev1 and 16M infected placentas but not in those from dams inoculated with Rev1Δwzm or 16MΔwzm mutants (FIG. 10). All these results indicated that Rev1Δwzm or 16MΔwzm mutants were safer in pregnant mice than both virulent and vaccine reference strains.

TABLE 5

Spleen, placental and foetal infections, and term pregnancies in CD1 mice infected with Rev1Δwzm, 16MΔwzm, Rev1 or 16M, at day 4.5 of pregnancy and slaughtered 15 days later.

| | | Spleen | | Pregnancy | Placenta | | Fetuses | |
| --- | --- | --- | --- | --- | --- | --- | --- | --- |
| Strain B. melitensis | Inoculation Dose/route | log CFU/ spleen | Spleen weight (grams) | No. of pregnant/ total dams | No. of dams with infected placentas/ pregnant | log CFU/ gram of placenta* | No. of dams with infected fetuses/pregnant | log CFU/ gram of fetuses* |
| Rev1 (vaccine) | 6.0 × $10^5$/IP | 5.70 ± 0.80 | 0.89 ± 0.29 | 10/14 | 10/10 | 8.5 ± 0.8 | 10/10 | 6.71 ± 0.49 |
| Rev1Δwzm | 6.3 × $10^5$/IP | 4.70 ± 0.80 | $0.30^1$ ± 0.80 | 12/14 | 0/12 | 1.52 ± 0* | 0/5 | 1.52 ± $0^a$ |
| 16M (virulent) | 6.9 × $10^5$/IP | 4.10 ± 0.50 | 0.83 ± 0.43 | 4/14 | 4/4 | 6.0 ± 1.42 | 2/2 | 6.16 ± 1.21 |
| 16MΔwzm | 6.5 × $10^5$/IP | 3.60 ± 0.70 | $0.16^1$ ± 0.08 | 5/7 | 0/5 | 1.32 ± 0* | 0/5 | 1.52 ± $0^a$ |

IP: intraperitoneal;
$^a$p < 0.001 vs. 16M (virulent) or Rev1 (vaccine) infected mice;
*Limit of Detection = 1.52 logs (i.e. no CFU isolated).

Example 14

Rev1 Δwzm and 16MΔwzm Confer Solid Protection Against S And R Virulent Infections in Mice, Equivalent or Better Than That Conferred by Rev1

Vaccine efficacy of the BrucellaΔwzm mutants was evaluated in 8-10 week-old female BALB/c mice (n=5) by intraperitoneal or subcutaneous vaccination with ≈$10^8$ CFU/mouse of the corresponding mutant. Mice (n=5) vaccinated subcutaneously with 2×$10^5$ CFU/mouse of Rev1 or S19 were used as reference vaccinated controls against either B. melitensis H38 and B. ovis PA or B. abortus infections, respectively. Three groups of mice (n=5) inoculated with 0.1 mL of sterile PBS were used as non-vaccinated controls in the corresponding experiment. Four weeks after vaccination, all mice were challenged intraperitoneally with 1×$10^4$ CFU/mouse of B. melitensis H38::$Gm^r$, 2×$10^5$ CFU/mouse of B. ovis BoPA::$Gm^r$ or 5×$10^4$ CFU/mouse of B. abortus 2308::$Gm^r$, challenge strains resistant to 15 μg/mL of gentamycin ($Gm_{15}$). Finally, the number of virulent bacteria in the spleens were determined at 2 (H38::$Gm^r$ and 2308::$Gm^r$) and 3 (BoPA::$Gm^r$) weeks after the challenge by plating each spleen onto BAB-S-$Gm_{15}$.

As can be seen in Table 6A, both Rev1Δwzm and 16MΔwzm::gfp mutants showed a degree of protection against a B. melitensis virulent infection similar to that showed by the Rev1 reference vaccine strain, not only by intraperitoneal but also by subcutaneous vaccination. Moreover, both B. melitensis Δwzm mutants conferred a superior protection against B. ovis infection (p<0.001) to that conferred by the Rev1 strain. In contrast, surprisingly, the Δwzm mutation in both B. abortus 2308Δwzm and S19Δwzm strains did not confer adequate protection against B. abortus virulent infection in mice (Table 6B).

TABLE 6A

Efficacy of vaccination against virulent infection by B. melitensis H38 (S-LPS virulent strain) or B. ovis PA (R-LPS virulent strain).

| | Vaccination Dose/route | log H38/spleen (mean ± SD) | Challenge H38::$Gm^r$ Uninfected[a]/totals | UP[b] | Challenge B. ovis log PoPA/spleen (mean ± SD) | PA::$Gm^r$ Uninfected/totals[a] | UP[b] |
|---|---|---|---|---|---|---|---|
| Rev1Δwzm | $10^8$/IP | 1.44 ± 1.28[c] | 3/5 | 4.32 | 0.7 ± 0.00[a] | 5/5 | 5.37 |
| | $10^8$/SC | 1.93 ± 1.43[c] | 2/5 | 3.83 | ND | | |
| 16M Δwzm::gfp | $10^8$/IP | 1.75 ± 1.52[c] | 3/5 | 4.01 | 0.62 ± 0.05[a] | 5/5 | 5.45 |
| | $10^8$/SC | 2.05 ± 1.00[c] | 1/5 | 3.71 | 1.91 ± 1.76[a] | 2/5 | 4.16 |
| Rev1 | 2 × $10^5$/SC | 1.38 ± 1.16[c] | 3/5 | 4.37 | 2.58 ± 1.88[a] | 2/5 | 3.49 |
| PBS Control | — | 5.76 ± 0.58[c] | 0/5 | — | 6.07 ± 0.24[a] | 0/5 | |

IP: intraperitoneal;
SC: subcutaneous;
[a]<5CFU/spleen;
[b]Units of Protection − log CFU/spleen in unvaccinated control − in test group;
[c]p < 0.001 vs. PBS control by PLSD test.
ND: Not Determined

TABLE 6B

Efficacy of vaccination with 2308Δwzm or S19Δwzm against virulent infection by B. abortus2308::$Gm^R$ (S-LPS virulent strain)

| | | Challenge 2308::$Gm^r$ | |
|---|---|---|---|
| Vaccine strain | Vaccination Dose/route | log 2308/spleen (mean ± SD) | Uninfected/totals* |
| 2308Δwzm | $10^8$/IP | 2.97 ± 1.41 [b] | 1/5 |
| | $10^8$/SC | 4.13 ± 1.08 | 0/5 |
| S19Δwzm | $10^8$/IP | 4.18 ± 1.91 | 0/5 |
| S19 | $10^5$/SC | 1.57 ± 1.96 [a] | 4/5 |
| PBS Control | — | 5.87 ± 0.26 | 0/5 |

IP: intraperitoneal;
SC: subcutaneous;
*<5 CFU/spleen;
**Units of Protection = log CFU/spleen in unvaccinated control − in tested group;
[a] p < 0.001;
[b] p < 0.05 vs. PBS control by PLSD test

Example 15

Serological Response of Lambs Inoculated with Rev1Δwzm:gfp or 16MΔwzm::gfp vs. Rev1::gfp Rasa Aragonesa male and female breed lambs born in the experimental flock of the Centro de Investigación y Tecnologia Agroalimentaria (CITA) del Gobierno de Aragón (Zaragoza, Spain) were used in these experiments, at 3-4 months of age. These animals were housed in the authorized facilities of the CITA (registration number ES/50-2970-12005), handled and manipulated according to the FELASA (www.felasa.eu) and ARRIVE (Kilkenny et al., 2010. PLoS Biology, 8: e1000412) recommendations.

Lambs were vaccinated by subcutaneous inoculation of a suspension containing 1-2×$10^{10}$ CFU of Rev1Δwzm::gfp (n=14) or 16MΔwzm::gfp (n=8). Groups of lambs non-vaccinated (n=13) or vaccinated with 1-2×$10^9$ CFU of Rev1::gfp (n=12) were used as controls. Thereafter, innocuousness was assessed by clinical inspection (rectal body temperature and palpation of the inoculation site) for one month after vaccination, and by periodical examination of epididymis and testicles all throughout the experiment. Moreover, blood samples were taken just before vaccination and, thereafter, weekly or every two weeks, by jugular vein puncture by using Venojet® (Terumo) vacuum tubes. After draining at room temperature for 24 h, blood samples were centrifuged at 3,500 rpm for 10 minutes and the resultant serum was conserved at −20° C. until its analysis.

The anti-LPS response was measured using a standard Rose Bengal Test (sRBT) and Complement Fixation Test (CFT), recommended by the WHO/OIE. Additionally, Gel Diffusion Tests (GDT) with R-LPS antigen was carried out in order to assess by seroconversion that vaccination was effective. Details on these serological tests can be found in the "*Manual of diagnostic tests and vaccines for terrestrial animals*" of the World Organization for Animal Health (OIE, 2016). An ELISA for anti-GFP antibodies in the serum was also performed on samples obtained from the serum of the lambs inoculated with 16MΔwzm::gfp.

Figure 11:
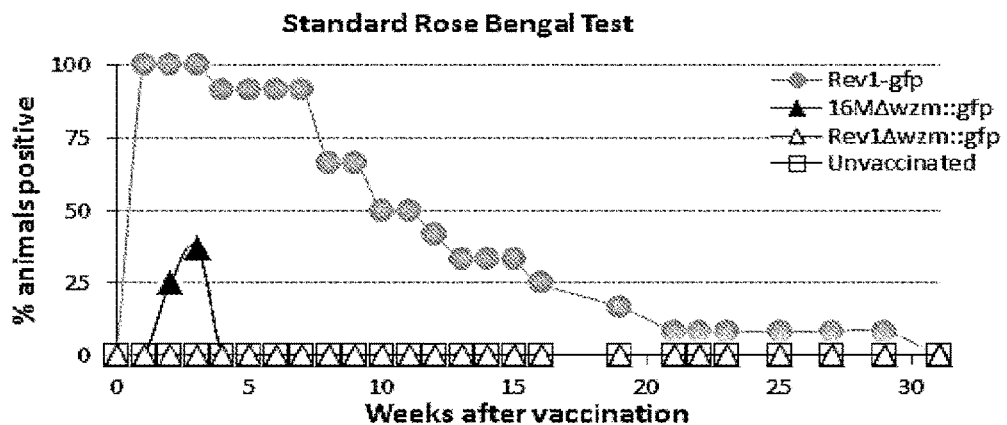
FIG. 11: Serological response against *Brucella* LPS in sheep vaccinated with Rev1Δwzm::gfp or 16MΔwzm::gfp. Lambs 3-4 months-old were vaccinated subcutaneously with 1-$2\times10^{10}$ CFU of Rev1Δwzm::gfp (n=14) or 16MΔwzm::gfp (n=8). Groups of lambs non-vaccinated (n=13) or vaccinated with 1-$2\times10^9$ CFU of Rev1::gfp (n=12) were used as controls. Innocuousness was assessed during the first month after vaccination by clinical inspection (rectal body temperature and palpation of the inoculation site) and testicles palpation. Serum samples were taken periodically for serological analysis by (A) standard Rose Bengal (sRBT); (B) Complement Fixation (CFT); (C) Gel Diffusion Tests against R-LPS antigen (GDT-R/LPS) and (D) anti-GFP ELISA tests (only for lambs vaccinated with 16MΔwzm::gfp).
Figure 11:
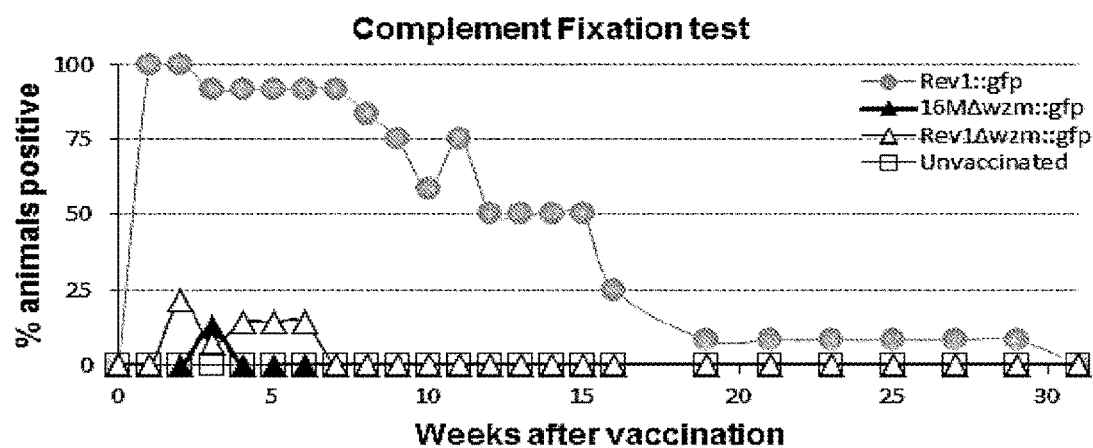
Figure 11:
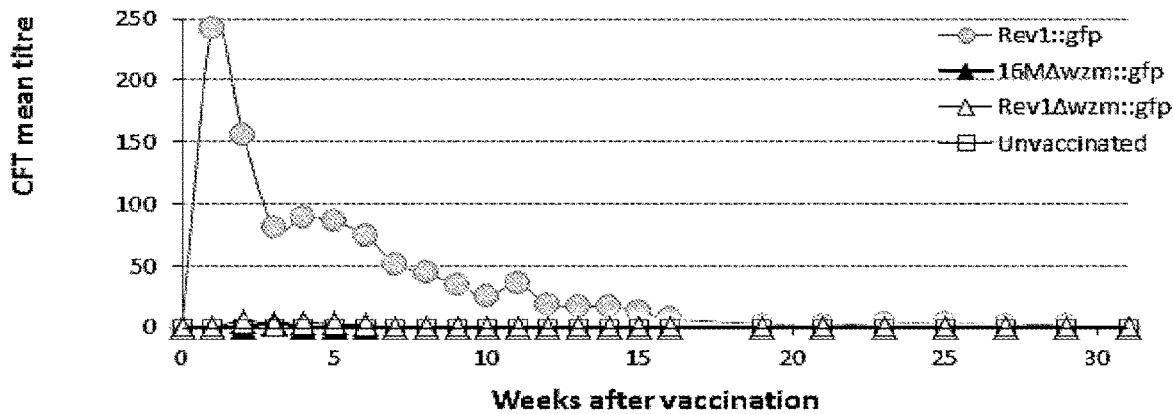
Figure 11:
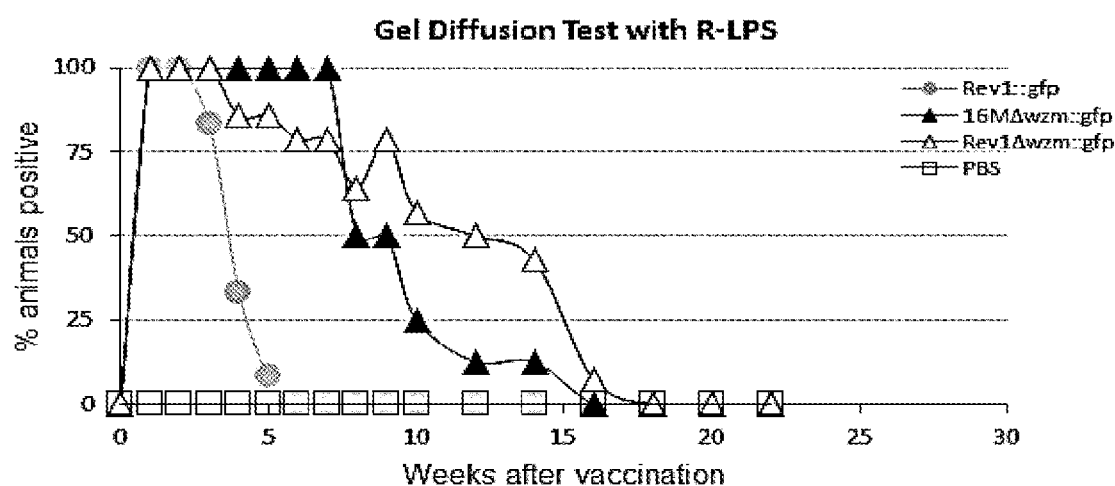
Figure 11:
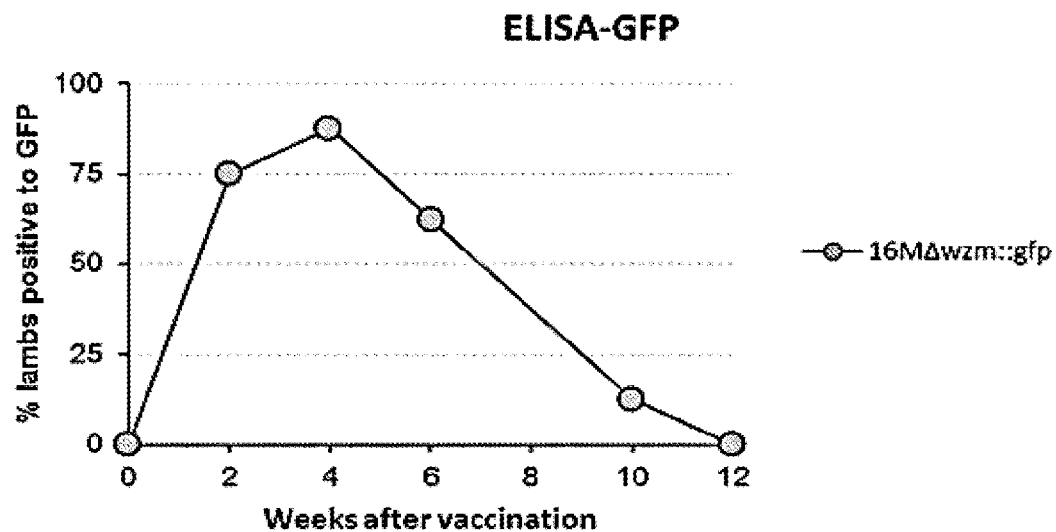

FIGS. 11A and 11B show that, in contrast to Rev1::gfp, vaccination with Rev1Δwzm::gfp or 16MΔwzm::gfp induced (if any) minimal serological interference in S-LPS *Brucella* tests. In fact, the serological response induced by Rev1Δwzm vaccination did not produce any interference in the sRBT (FIG. 11A) and only three lambs elicited anti-S/LPS antibodies detectable by CFT. In contrast, three animals vaccinated with 16MΔwzm::gfp were positive in sRBT (FIG. 11A) and one of them was also positive in CFT. In any case, these four CFT positive lambs vaccinated with the Δwzm mutants showed very low anti-S/LPS titres, which persisted for less than 6 weeks post-vaccination (FIG. 11B). The 100% animals positive in GDT-R/LPS (FIG. 11C) demonstrated that all lambs were correctly vaccinated with the Rev1Δwzm::gfp or 16MΔwzm::gfp mutant, indicating that the absence of S/LPS-reactions would be due to the nature of O-PS accumulated in Δwzm mutants.

FIG. 11D shows that lambs which were inoculated with 16MΔwzm::gfp also produced antibodies that bind to GFP. These antibodies could be used in a serological test to discriminate between vaccinated and infected lambs. Further, this sort of test could also be used to discriminate between lambs inoculated with Rev1Δwzm::gfp and infected lambs.

Example 16

Efficacy of Rev1Δwzm:gfp Vaccination Against a *B. Ovis* PA Experimental Infection in Rams Rasa Aragonesa male and female breed lambs born in the experimental flock of the Centro de Investigación y Tecnologia Agroalimentaria (CITA) del Gobierno de Aragón (Zaragoza, Spain) were used in these experiments, at 3-4 months of age. These animals were housed in the authorized facilities of the CITA (registration number ES/50-2970-12005), handled and manipulated according to the FELASA (www.felasa.eu) and ARRIVE (Kilkenny et al., 2010. PLoS Biology, 8: e1000412) recommendations.

Lambs (n=14) were vaccinated by subcutaneous injection of 1-2×$10^{10}$ CFU of Rev1Δwzm::gfp. One group (n=13) kept unvaccinated were used as control. Thereafter, innocuousness was assessed by clinical inspection (rectal body temperature and palpation of the inoculation site) for one month after vaccination, and by periodical examination of epididymis and testicles all throughout the experiment. At 8 months after vaccination, all lambs were experimentally challenged with 2×$10^9$ CFU de *B. ovis* PA by conjunctival and preputial routes (30 μL/each route) and slaughtered 2 months later for bacteriological purposes. Samples of spleens, epididymis, seminal vesicles and cranial, prescapular, crural, iliac and scrotal lymph nodes were taken, homogenized in sterile PBS and cultured by duplicate in CITA medium (De Miguel et al. 2011. Journal of Clinical Microbiology. 49(4): 1458-1463). The number and percentage of infected animals and samples were determined as previously described (Grilló et al. 2009. Vaccine, 27: 187-191) and the mean infection index was calculated as the sum of the infection levels assigned to each sample divided by all the samples processed from each group. The infection level was assigned as follows: 1 (1-5 CFU), 2 (6-25 CFU); 3 (26-125 CFU); 4 (126-300 CFU); 5 (>300 CFU). The statistical comparisons of percentages and means were performed by the Chi-square and Kruskal-Wallis tests, respectively.

As shown in Table 7, vaccination of lambs at 3-4 months of age with Rev1Δwzm::gfp induces significant protection against a challenge infection by *B. ovis* PA at 11-12 months of age, regarding not only the number of animals found infected but also the number of samples detected as infected by *B. ovis* PA. Moreover, the level of infection observed in both vaccine groups were lower than that observed in the unvaccinated control group.

TABLE 7

Efficacy against *B. ovis* PA infection in rams vaccinated with Rev1Δwzm::gfp at 3-4 months old.

| Vaccination group[1] | No. (%) Infected/total animals | No. (%) Infected/ total samples | Mean Infection Index [2] |
|---|---|---|---|
| Rev1Δwzm::gfp | 5/14 (35.7%) [a] | 15/112 (13.4%) [b] | 0.29 |
| Unvaccinated | 12/13 (92.3%) | 47/104 (45.2%) | 1.00 |

[1]Male lambs of 3-4 months old were vaccinated subcutaneously with 2 × $10^{10}$ CFU of Rev1Δwzm::gfp, challenged 8 months post-vaccination, and analyzed by bacteriology 2 months after challenge;
[2] Mean Infection Index = the sum of the infection levels assigned to each sample divided by all the samples processed from each group;
Statistical comparisons:
[a] $p = 0.002$;
[b] $p < 0.0001$.

Example 17

Immune Sera from Lambs Vaccinated with Rev1Δwzm are Effective Against *B. melitensis* H38 And *B. Abortus* 2308 S-LPS Virulent Strains Exponentially grown *B. melitensis* H38, *B. abortus* 2308 and *B. ovis* PA were adjusted to $10^4$ CFU/mL in PBS and mixed, in triplicate in microtiter plates (45 μL/well), with 90 μL/well of normal or heat-treated (1 h, 56° C.) sera extracted from lambs showing anti-R/LPS antibodies in GDT-R/LPS (one of them was positive in CFT as well) at 2 weeks after inoculation with Rev1Δwzm. After 18 h of incubation at 37° C., and 10% $CO_2$ for *B. ovis,* 65 μL of TSB were dispensed into each well, the bacterial suspension was mixed, and 50 μL were plated on BAB in triplicate. The results were expressed as the standardized percentage of bacteria counts with respect to initial count in the inocula. As it can be seen in the FIG. 12, the immune sera from lambs treated with Rev1Δwzm were capable of killing either *B. melitensis* H38, *B. abortus* 2308 or *B. ovis* PA.

The invention claimed is:

1. A vaccine composition comprising a modified *Brucella melitensis* Rev1 strain, wherein the wzm gene has been inactivated, and a pharmaceutically acceptable carrier, diluent and/or adjuvant.

2. The vaccine composition according to claim 1, wherein the wzm gene has been partially deleted.

3. The vaccine composition according to claim 1, wherein the wzm gene has been completely deleted.

4. The vaccine composition according to claim 1, wherein the wild type wzm gene has the nucleotide sequence of SEQ ID NO: 1.

5. The vaccine composition according to claim 4, wherein at least 50% of SEQ ID NO: 1 has been deleted.

6. The vaccine composition according to claim 4, wherein at least 60% of SEQ ID NO: 1 has been deleted.

7. The vaccine composition according to claim 4, wherein at least 70% of SEQ ID NO: 1 has been deleted.

8. The vaccine composition according to claim 4, wherein at least 80% of SEQ ID NO: 1 has been deleted.

9. The vaccine composition according to claim 4, wherein nucleotides 80-721 of SEQ ID NO: 1 have been deleted.

10. The vaccine composition according to claim 1, wherein the strain has been further modified to express a fluorescent protein.

11. The vaccine composition according to claim 10, wherein the fluorescent protein is green fluorescent protein (GFP).

12. The vaccine composition according to claim 1, wherein the strain has been lyophilized.

* * * * *